United States Patent
Campbell et al.

(10) Patent No.: US 6,201,168 B1
(45) Date of Patent: Mar. 13, 2001

(54) PATHOGENESIS OF CARDIOMYOPATHY

(75) Inventors: Kevin P. Campbell; Ramon Coral; Ronald Cohn; Roger Williamson; Madeleine Durbeej, all of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/378,418

(22) Filed: Aug. 20, 1999

(51) Int. Cl.[7] .................. A01K 67/027; G01N 33/00
(52) U.S. Cl. ........................... 800/18; 800/3; 800/9
(58) Field of Search .......................... 800/8, 3, 18, 9

(56) References Cited

U.S. PATENT DOCUMENTS 5,672,694  *  9/1997  Campbell et al. ............... 536/22.1

OTHER PUBLICATIONS

Duclos F. The Journal of Cell Biol. 142: 1461–1471, 1998.*
Araishi K et al. Human Molecular Genetics. 8: 1589–1598, Sep., 1999.*
Durbeej M et al. Molecular Cell 5: 141–151, 2000.*
Campbell and Kahl, *Nature* 338: 259–362 (1989).
Yoshida and Ozawa, *J. Biochem.* 108: 748–752 (1990).
Crosbie et al., *J. Cell Biol.* 145: 153–165 (1999).
Duclos et al., *Neuromusc. Disord.* 8: 30–38 (1998).
Holt et al., *Mol. Cell* 1: 841–848 (1998).
Straub et al., *Am. J. Path.* 153: 1623–1630 (1998).
Towbin, J.A., *Curr. Opin. Cell Biol.* 10: 131–139 (1998).
Melacini et al., *Muscle & Nerve* 22: 473–479 (1999).
Badorff et al., *Nat. Med.* 5: 320–326 (1999).
Moreira et al., *J. Med. Genet.* 35: 951–953 (1998).
Hack et al., *J. Cell Biol.* 142: 1279–1287 (1998).
Sakamoto et al., *FEBS Letters* 447: 124–128 (1999).
Kaski, J.C., *Cardiovasc. Drugs Ther.* 9: 221–227 (1995).
Kukovetz et al., *J. Cardiovasc. Pharmacol.* 20 (Suppl.3): S1–S7 (1992).
Fewell et al., *Am. J. Physiol.* 273: H1595–H1605 (1997).
Bönnemann et al., *Neuromusc. Disord.* 8: 193–197 (1998).
Ettinger et al., *J. Biol. Chem.* 272: 32534–32538 (1997).
McNally et al., *FEBS Lett.* 422: 27–32 (1998).

* cited by examiner

*Primary Examiner*—Karen M. Hauda
*Assistant Examiner*—Ram R. Shukla
(74) *Attorney, Agent, or Firm*—Kevin M. Farrell

(57) ABSTRACT

Disclosed is a mouse, cells derived therefrom, and methods for using the mouse, the mouse being homozygous for a disrupted δ-sarcoglycan gene, the disruption in the gene having been introduced into the mouse or an ancestor of the mouse at an embryonic stage. The disruption prevents the synthesis of functional δ-sarcoglycan in cells of the mouse and results in the mouse having a reduced amount of β- and ε-sarcoglycan and sarcospan, and a disruption of the sarcoglycan-sarcospan complex in smooth muscle of the mouse. Also disclosed is a mouse, cells derived therefrom, and methods for using the mouse, the mouse being homozygous for a disrupted β-sarcoglycan gene, the disruption in the gene having been introduced into the mouse or an ancestor of the mouse at an embryonic stage. The disruption prevents the synthesis of functional β-sarcoglycan in cells of the mouse and results in the mouse having a reduced amount of δ-and ε-sarcoglycan and sarcospan and α-dystroglycan in smooth muscle of the mouse.

13 Claims, 2 Drawing Sheets

SEQUENCE LISTING

<160> NUMBER OF SEQ ID NOS: 5

<210> SEQ ID NO 1
<211> LENGTH: 18
<212> TYPE: DNA
<213> ORGANISM: Hamster sp.

<400> SEQUENCE: 1
agctcagagg ggccacac                                                      18

<210> SEQ ID NO 2
<211> LENGTH: 20
<212> TYPE: DNA
<213> ORGANISM: Mouse sp.

<400> SEQUENCE: 2
cagccagtgt ttcaagccaa                                                    20

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      sequence from targeting vector for genotyping offspring via PCR

<400> SEQUENCE: 3
gctatcagga catagcgttg gcta                                               24

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence:
      sequence from targeting vector for genotyping offspring via PCR

<400> SEQUENCE: 4
gcaaacttgg agagtgaaga ggc                                                23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:
      sequence from targeting vector for genotyping offspring via PCR

<400> SEQUENCE: 5
gaggcatata aagtttgcac gac                                                23

PATHOGENESIS OF CARDIOMYOPATHY

BACKGROUND OF THE INVENTION

The sarcoglycan complex is a group of single pass transmembrane proteins (α-, β-, ι- and γ-sarcoglycan) which is tightly associated with sarcospan to form a subcomplex within the dystrophin-glycoprotein complex (DGC) in skeletal and cardiac muscle (Campbell et al., *Nature* 338: 259–362 (1989); Yoshida et al., *J. Biochem.* 108: 748–752 (1990); Crosbie et al., *J. Cell Biol.* 145: 153–165 (1999)). The DGC is further comprised of dystrophin, the dystroglycan complex and the syntrophins (Hoffman et al., *Cell* 51: 919–928 (1987); Froehner et al., *Soc. Gen. Physiol. Ser.* 52: 197–207 (1997); Durbeej et al., *Curr. Opin. Cell. Biol.* 10: 594–601 (1998)). The expression of the sarcoglycan-sarcospan complex is necessary to target dystroglycan to the sarcolemma (Duclos et al., *J. Cell Biol.* 142: 1461–1471 (1998); Duclos et al., *Neuromusc. Disord.* 8: 30–38 (1998); Holt et al., *Mol. Cell* 1: 841–848 (1998); Straub et al., *Am. J. Path.* 153: 1623–1630 (1998)) which in turn confers a link between the extracellular matrix and the F-actin cytoskeleton (Ervasti et al., *J. Cell Biol.* 122: 809–823 (1993)). Thus, the DGC is thought to protect muscle cells from contraction-induced damage (Petrof et al., *Proc. Natl. Acad. Sci. USA* 90: 3710–3714 (1993)). In agreement with this hypothesis, mutations in the genes for the sarcoglycans, dystrophin and laminin α2 chain are responsible for limb-girdle muscular dystrophy, Duchenne/Becker muscular dystrophy and congenital muscular dystrophy respectively (Straub et al., *Curr. Opin. Neurol.* 10: 168–175 (1997); Lim et al., *Curr. Opin. Neurol.* 11: 443–452 (1998)). Clinical evidence of cardiomyopathy is variably present in these muscular dystrophies (Towbin, J. A., *Curr. Opin. Cell Biol.* 10: 131–139 (1998)) but a correlation between the primary mutation of the sarcoglycan genes and cardiomyopathy is yet to be established (Melacini et al., *Muscle & Nerve* 22: 473–479 (1999)).

Dilated cardiomyopathy is a multifactorial disease that includes both inherited and acquired forms of cardiomyopathy. Inherited cardiomyopathy in humans can be associated with genetic defects occurring in components of the dystrophin-glycoprotein complex (DGC) (Towbin, J. A., *Curr. Opin. Cell Biol.* 10: 131–139 (1998)). Mutations in the dystrophin gene lead to a high incidence of cardiomyopathy in Duchenne and Becker muscular dystrophy patients (DMD/BMD) and can cause X-linked dilated cardiomyopathy (Towbin, J. A., *Curr. Opin. Cell Biol.* 10: 131–139 (1998)). In addition to these primary genetic causes of cardiomyopathy, recent data suggest that disruption of the DGC underlie the cardiomyopathy associated with enteroviral infection (Badorff et al., *Nat. Med.* 5: 320–326 (1999)). Consequently, evidence is accumulating that the DGC plays a critical role in the pathogenesis of some forms of inherited and acquired cardiomyopathy. Several components of the DGC are also expressed in smooth muscle (Houzelstein et al., *J. Cell Biol.* 119: 811–821 (1992); North et al., *J. Cell Biol.* 120: 1159–1167 (1993); Ozawa, et al., *Hum. Mol. Gen.* 4: 1711–1716 (1995); Durbeej et al., *Curr. Opin. Cell. Biol.* 10: 594–601 (1998)). Interestingly, potential smooth muscle dysfunction has been described in patients with Duchenne muscular dystrophy (Bahron et al., *N. Engl. J. Med.* 319: 15–18 (1998); Jaffe et al., *Arch. Phys. Med. Rehabil.* 71: 742–744 (1990)). However, no smooth muscle dysfunction has been reported in patients with limb-girdle muscular dystrophy.

Recently, a fifth sarcoglycan, ε-sarcoglycan, was cloned and shown to be highly homologous to α-sarcoglycan (Ettinger et al., *J. Biol. Chem.* 272: 32534–32538 (1997); McNally et al., *FEBS Lett.* 422: 27–32 (1998)). ε-sarcoglycan is expressed in skeletal and cardiac muscle, but also in several non-muscle tissues. Whether ε-sarcoglycan is associated with the other sarcoglycans in striated muscle is yet to be determined. At the immunofluorescence level, however, it has been shown that ε-sarcoglycan is still present in skeletal muscle of a-sarcoglycan deficient (Sgca-null mice) mice although the other sarcoglycans are greatly reduced (Duclos et al., *J. Cell Biol.* 142: 1461–1471 (1998)). This indicates that ε-sarcoglycan is not an additional member of the known tetrameric complex of α-, β-, γ- and δ-sarcoglycan in skeletal muscle but may be part of a distinct complex at the sarcolemma.

Sgca-null mice have recently been reported to display a progressive muscular dystrophy (Duclos et al., *J. Cell Biol.* 142: 1461–1471 (1998)). The primary absence of α-sarcoglycan was accompanied by the concomitant loss of β-,γ- and δ-sarcoglycan and sarcospan in skeletal and cardiac muscle fibers, a phenomenon that is also observed in human forms of sarcoglycanopathies (Lim et al., *Curr. Opin. Neurol.* 11: 443–52 (1998)). Interestingly, although the SG-SSPN complex was absent from the cardiac muscle membrane, no morphological signs of cardiomyopathy were observed (Duclos et al., *J. Cell Biol.* 142: 1461–1471 (1998)).

SUMMARY OF THE INVENTION

One aspect of the present invention relates to a mouse, and cells derived therefrom, which is homozygous for a disrupted δ-sarcoglycan gene, the disruption in said gene having been introduced into the mouse or an ancestor of the mouse at an embryonic stage. Said disruption prevents the synthesis of functional δ-sarcoglycan in cells of the mouse and results in the mouse having a reduced amount of β- and ε-sarcoglycan and sarcospan, and a disruption of the sarcoglycan-sarcospan complex in smooth muscle of the mouse. Said disruption also results in a reduced amount of sarcospan, α-, β-, β-, and ε-sarcoglycan in the sarcolemma of skeletal and cardiac muscles of the mouse, compared to the amounts of said components in a mouse lacking disrupted δ-sarcoglycan genes. Preferred specific disruptions of the δ-sarcoglycan gene are listed.

Another aspect of the present invention relates to a mouse, and cells derived therefrom, which is homozygous for a disrupted β-sarcoglycan gene, the disruption in said gene having been introduced into the mouse or an ancestor of the mouse at an embryonic stage. The disruption prevents the synthesis of functional β-sarcoglycan in cells of the mouse and results in the mouse having a reduced amount of 6- and ε-sarcoglycan and sarcospan and α-dystroglycan in smooth muscle of the mouse. The disruption also results in a disruption of the sarcoglycan-sarcospan complex in smooth muscle of the mouse, and a reduced amount of sarcospan, α-, γ-, δ- and ε-sarcoglycan in the sarcolemma of skeletal and cardiac muscles of the mouse, compared to the amounts of the components in a mouse lacking disrupted β-sarcoglycan genes. Preferred specific disruptions of the β-sarcoglycan gene are listed.

Another aspect of the present invention is a method for treating mammalian autosomal recessive limb-girdle muscular dystrophy type 2F in an individual. The method comprises, providing an expression vector which encodes a wild-type form of δ-sarcoglycan, and introducing the expression vector into skeletal and smooth muscle tissue of the individual under conditions appropriate for expression of the wild-type form of δ-sarcoglycan in said tissues. Examples of expression vectors for use in this method are adenovirus expression vector, a gutted adenovirus expression vector, and an adeno-associated expression vector. In one embodiment, the expression vector contains a muscle tissue-specific promoter. One method of introduction into the skeletal muscle is by intramuscular injection.

Another aspect of the present invention is a method for treating mammalian autosomal recessive limb-girdle muscular dystrophy type 2E in an individual. The method comprises, providing an expression vector which encodes a wild-type form of β-sarcoglycan, and introducing the expression vector into skeletal and smooth muscle tissue of the individual under conditions appropriate for expression of the wild-type form of β-sarcoglycan in said tissues. Examples of expression vectors for use in this method are adenovirus expression vector, a gutted adenovirus expression vector, and an adeno-associated expression vector. In one embodiment, the expression vector contains a muscle tissue-specific promoter. One method of introduction into the skeletal muscle is by intramuscular injection.

The δ-sarcoglycan deficient, and β-sarcoglycan deficient mice of the present invention are useful in identifying therapeutic compounds for treatment of an individual diagnosed with δ-sarcoglycan-deficient limb-girdle muscular dystrophy, and δ-sarcoglycan-deficient limb-girdle muscular dystrophy, respectively.

Another aspect of the present invention is a therapeutic method for treating ischemic heart disease caused by reduced expression of the sarcoglycan-sarcospan complex in vascular smooth muscle cells of an individual. The method comprises contacting the vascular smooth muscle cells of the individual with a vascular smooth muscle relaxant, such as Nicorandil. Such reduced expression of the sarcoglycan-sarcospan complex in vascular smooth muscle cells of the individual may be due to a defect in the δ-sarcoglycan genes of the individual, or to a defect in the β-sarcoglycan genes of the individual. This method is also useful for preventing ischemic injury in skeletal and cardiac muscle of an individual caused by reduced expression of the sarcoglycan-sarcospan complex in the vascular smooth muscle cells of the individual. The method is also useful for treating mammalian autosomal recessive limb-girdle muscular dystrophy type 2F or type 2E in an individual. Other methods provided include methods for identifying a therapeutic compound for the treatment of ischemic heart disease in an individual caused by reduced expression of the sarcoglycan-sarcospan complex in the vascular smooth muscle cells of the individual, and also method for identifying a therapeutic compound for the prevention of ischemic injury in skeletal and cardiac muscle of an individual which is caused by reduced expression of the sarcoglycan-sarcospan complex in vascular smooth muscle cells of the individual.

DETAILED DESCRIPTION OF THE INVENTION

Figure 1:
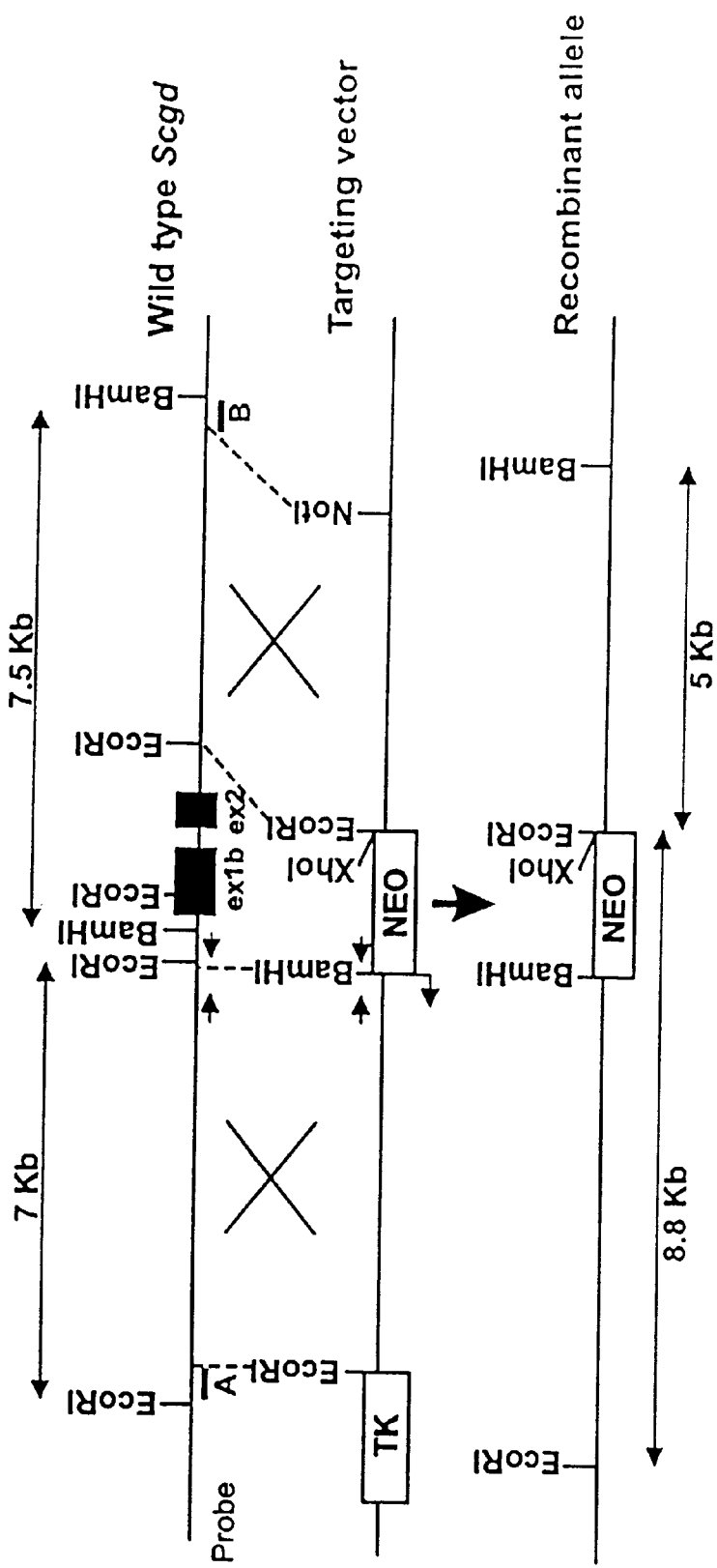
FIG. 1 is a schematic representation of targeted disruption of the mouse Sgcd-gene. Shown is a restriction map of the 5' portion of the Sgcd-gene showing wild type allele (top), the targeting vector (middle), and the predicted targeted allele following homologous recombination (bottom) The position of the neo and tk cassettes, hybridization sites of probes A and B, for Southern analyses, and the primers used for PCR-based genotyping (→) are indicated.

Aspects of the present invention are based upon the generation and study of Sgcd-null mice (δ-sarcoglycan knockout), and Sgcb-null (β-sarcoglycan knockout) mice. The homozygous disruption of either of these genes in the mouse results in an absence of the sarcoglycan-sarcospan (SG-SSPN) complex in skeletal and cardiac membranes and also the loss of a newly identified unique vascular smooth muscle SG-SSPN complex. Surprisingly, the disruption of the SG-SSPN complex in vascular smooth muscle of the mice perturbs vascular function, which initiates cardiomyopathy and exacerbates muscular dystrophy.

Cardiomyopathy is a common clinical phenotype of patients with certain forms of limb-girdle muscular dystrophy. Cardiac involvement has been previously documented in patients with primary mutations of β-, γ- and δ-sarcoglycan (Moreira et al., *J. Med. Genet.* 35: 951–953 (1998); Melacini et al., *Muscle Nerve* 22: 473–479 (1999), RD Cohn and T. Voit, personal communication) while patients with mutations in the α-sarcoglycan gene (the most common form of sarcoglycanopathies) only rarely display mild forms of cardiomyopathy (Melacini et al., *Muscle Nerve* 22: 473–479 (1999)). However, prior to this disclosure, the involvement of the specific sarcoglycans in the pathogenesis of cardiomyopathy and muscular dystrophy, with respect to tissue distribution, was largely unknown.

One aspect of the present invention is a mouse, and cells derived therefrom, which is homozygous for a disrupted δ-sarcoglycan gene. The disruption in the δ-sarcoglycan gene is introduced into the mouse or an ancestor of the mouse at an embryonic stage. The introduced disruption necessarily prevents the synthesis of functional δ-sarcoglycan in all cells of the mouse. The molecular consequences of the mutation in the mouse includes, without limitation, a reduction in the amount of sarcospan, β- and ε-sarcoglycan in smooth muscle, and also a disruption of the sarcoglycan-sarcospan complex in smooth muscle. In addition, there is a reduced amount of sarcospan, α-, β-, γ-, and ε-sarcoglycan in the sarcolemma of skeletal and cardiac muscle of the mouse. The reduction in the amount of the aforementioned molecules are determined by comparison to the amounts of these molecules in the corresponding tissue of a mouse lacking a disrupted δ-sarcoglycan gene.

One of skill in the art will recognize that functional disruption of the δ-sarcoglycan gene can be achieved by several approaches. Generally, a specific disruption of the δ-sarcoglycan gene is made in a progenitor cell (embryonic stem cells) of the mouse. A mouse which is heterozygous for the disrupted gene is produced, and a mouse homozygous for the disrupted gene is produced by mating two heterozygotes. In one embodiment, the disruption in the δ-sarcoglycan gene results in a deletion of a region of 2992 base pairs, the region including 2277 base pairs of intron 1, the entire exon 2, and 576 base pairs of intron 2. This deleted region of the mouse genome is replaced with a PGK-neomycin cassette as a marker for neomycin resistance.

Such a disruption can be produced by introduction, into embryonic stem cells, of a DNA construct which has 5 kb of intron 1 and 5 kb of intron 2 of the wild type δ-sarcoglycan gene, but lacks exon 2, and instead has a neomycin resistance gene inserted between the sequences from intron 1 and intron 2 sequences, in the opposite transcriptional orientation as the exon 2 sequences which it is replacing.

Another aspect of the present invention is a mouse, and cells derived therefrom, which is homozygous for a disrupted β-sarcoglycan gene. The disruption in the β-sarcoglycan gene having been introduced into the mouse or an ancestor of the mouse at an embryonic stage. The disruption necessarily prevents the synthesis of functional β-sarcoglycan in all cells of the mouse. The molecular consequences of the mutation in the mouse includes, without limitation, a reduction in the amount of sarcospan, δ- and ε-sarcoglycan in smooth muscle, and also a disruption of the sarcoglycan-sarcospan complex in smooth muscle. In addition, there is a reduced amount of sarcospan, α-, δ-, γ-, and ε-sarcoglycan in the sarcolemma of skeletal and cardiac muscle of the mouse. The reduction in the amount of the aforementioned molecules are determined by comparison to the amounts of these molecules in the corresponding tissues of a mouse lacking a disrupted β-sarcoglycan gene.

One of skill in the art will recognize that functional disruption of the β-sarcoglycan gene can be achieved by several approaches. Generally, a specific disruption of a β-sarcoglycan gene is made in a progenitor (embryonic stem) cell of a mouse, a heterozygous mouse is produced, and homozygotes are generated by mating the heterozygotes. In one embodiment, the disruption in the is produced from a disruption results in a deletion of a region of about 7.5 kb, the region including 1606 bp of intron 2, the entirety of exons 3, 4, 5, 6, introns 3, 4, and 5, and also 498 bp immediately downstream of exon 6. This deleted region of the mouse genome is replaced with a PGK-neomycin cassette as a marker for neomycin resistance. Such a disruption can be produced by introduction, into embryonic stem cells, of a DNA construct which has 1800 bp of intron 2 and 6500 base pairs of sequences which begin 498 base pairs directly downstream of exon 6 of the wild type β-sarcoglycan gene, having a neomycin resistance gene inserted between these sequences at a position where the intervening sequences which are replaced are located in the wild type mouse genome.

Preliminary examination of the Sgcd-null and Sgcb-null mice reveals strikingly similar phenotypes. Both the Sgcd-null mice and the Sgcb-null mice develop a severe cardiomyopathy with focal areas of myocardial ischemic like-lesions as the characteristic histopathological feature, followed by fibrotic calcification and scarring of the cardiac muscle. This is in contrast to the previously generated Sgca-null mouse (Duclos et al., *J. Cell Biol.* 142: 1461–1471 (1998)) which exhibits no histopathological signs of cardiomyopathy, although the SG-SSPN complex was absent in the cardiac muscle membranes of this mouse. These findings are in accordance with the clinical data observed in patients with primary mutations in the α-sarcoglycan gene, which also do not or only mildly display cardiomyopathic phenotypes.

The most noticeable molecular difference between the Sgca-null mouse and the Sgcd-null mouse and Sgcb-null mouse of the present invention is expression of the SG-SSPN complex in smooth muscle cells of the vasculature. While the expression of the SG-SSPN complex is reduced at the sarcolemma of skeletal and cardiac muscle in all three mutants, compared to expression of these molecules in a wild type mouse, the expression of the sarcoglycan-sarcospan complex in smooth muscle cells of the blood vessels is disrupted in the Sgcd-null and the Sgcb-null mice, but not in the Sgca-null mice. These findings, together with observed characteristic ischemic-like lesions in cardiac and skeletal muscle of Sgcd-null and Sgcb-null mice, indicate that vascular dysfunction has an essential impact on the development of cardiomyopathy and on the severity of muscular dystrophy in these mutant mice. These observations indicate the existence of a novel mechanism in the pathogenesis of cardiomyopathy where disruption of the sarcoglycan-sarcospan complex in vascular smooth muscle perturbs vascular function, induces ischemic injury in cardiac and skeletal muscles, and leads to cardiomyopathy and muscular dystrophy exacerbation in human patients. The disclosed findings open up a new area of research into the functional role of the sarcoglycan-sarcospan complex in vascular smooth muscle and its involvement in coronary artery disease.

Applicants have previously demonstrated gene replacement therapy for the treatment of mammalian sarcoglycan deficient limb-girdle muscular dystrophy in Campbell et al., U.S. patent application Ser. No. 09/164,664, filed Oct. 1, 1998, currently pending, the contents of which are incorporated herein by reference. This previous disclosure demonstrated that sarcoglycan gene replacement therapy of a deficient sarcoglycan species into skeletal muscle cells of a patient produces extensive long-term expression of the deficient sarcoglycan species to restore the entire sarcoglycan complex, results in the stable association of α-dystroglycan with the sarcolemma, and eliminates the morphological markers of limb-girdle muscular dystrophy. The present invention indicates that additional therapeutic benefit can be produced in individuals having a deficiency of certain specific sarcoglycan species (e.g. δ-sarcoglycan, β-sarcoglycan, and possibly ε-sarcoglycan) from additionally directing gene replacement therapy towards smooth muscle cells, especially vascular smooth muscle cells, of the individual. Specifically, an individual suffering from a non-dominant deficiency of δ-sarcoglycan (e.g. mammalian autosomal recessive limb-girdle muscular dystrophy type 2F) is treated by introducing an expression vector encoding a wild-type form of δ-sarcoglycan into skeletal and smooth muscle tissue of the individual under conditions appropriate for expression of the gene in the different tissues. This method may optimally utilize two or more different expression vectors, to achieve the desired patterns of delivery and expression of the introduced δ-sarcoglycan gene. Expression vectors currently known in the art are include, without limitation, adenovirus based expression vectors, described by Gregory et al., (1997) U.S. Pat. No. 5,670,488; McClelland et al., (1998) U.S. Pat. No. 5,756,086; Armentano et al., (1998) U.S. Pat. No. 5,707,618; Saito et al., (1998) U.S. Pat. No. 5,731,172, the contents of each are incorporated herein by reference. Also included are gutted adenovirus delivery systems (Clemens et al., Gene Therapy 3: 965–972 (1996)), and adeno-associated virus (AAV) based vectors, some examples of which are described by Podsakof et al., (1999) U.S. Pat. No. 5,858,351; Carter et al., (1989) U.S. Pat. No. 4,797,368; Lebkowski et al., (1992) U.S. Pat. No. 5,153,414; Srivastava et al., (1993) U.S. Pat. No. 5,252,479; Lebkowski et al., (1994) U.S. Pat. No. 5,354,678; Wilson et al., (1998) U.S. Pat. No. 5,756,283, the contents of each being incorporated herein by reference. Other possible gene expression systems for sarcoglycan gene replacement therapy include retroviral based vectors and delivery systems (Miller et al., *Blood* 76, 271 (1990), Booth et al., (1995) U.S. Pat. No.

5,466,676, the contents of which are incorporated herein by reference, and also plasmid based nucleic acid delivery systems described by Eastman et al., (1998) U.S. Pat. No. 5,763,270, the contents of which are incorporated herein by reference.

The method of delivery of the gene expression system to the target tissue should result in direct contact of the gene expression system to the target tissue, and will vary with the expression system used and the target tissue. Common methods of delivery are intramuscular injection (e.g. for delivery to skeletal muscle), and intravenous administration (e.g. for delivery to vascular smooth muscle cells). Administration of the deficient sarcoglycan gene should optimally occur at as early a stage in disease progression as diagnosis permits, preferably, prior to the onset of severe muscle or cardiovascular damage. Genetic diagnosis of the disease prior to the onset of the pathology allows gene therapy intervention at an extremely early stage in life.

Preferably, tissue specific regulatory elements or promoter elements are utilized in the expression vector(s). Optimally, the regulatory elements are specific for expression in muscle, and may further be specific for skeletal muscle or smooth muscle. Examples of such tissue specific regulatory elements and methods of use in gene therapy are described in Ordahl et al., (1993) U.S. Pat. No. 5,266,488, and Olson et al., (1998) U.S. Pat. No. 5,837,534, the contents of each being incorporated herein by reference.

An individual suffering from a non-dominant deficiency of β-sarcoglycan (e.g. mammalian autosomal recessive limb-girdle muscular dystrophy type 2E) is likewise treated by introducing an expression vector encoding a wild-type form of β-sarcoglycan into skeletal and smooth muscle tissue of the individual, by the above described methods.

The development of the Scgd-null and Scgb-null mice provides animal models for the human conditions of autosomal recessive limb-girdle muscular dystrophy type 2F and 2E, respectively, and also for ischemic heart disease which is associated with a reduction in expression of the sarcoglycan-sarcospan complex in the vascular smooth muscle cells of an individual. These animal models more closely parallel the human disease condition than animal models previously known. Recently, Hack and colleagues (Hack et al., *J. Cell Boil*. 142: 1279–1287 (1998)) reported that mice deficient in γ-sarcoglycan develop cardiomyopathy. The authors described primarily fibrotic changes in the ventricular wall. However, there was no report of initial acute necrotic areas in cardiac muscle and the authors suggested that the cardiomyopathy might be secondary to dystrophic changes of the diaphragm. Another animal model, the BIO 14.6 cardiomyopathic hamster, which has been shown to have a genomic deletion in the δ-sarcoglycan gene (Sakamoto et al., *FEBS Letters* 447: 124–128 (1999)), displays cardiac abnormalities similar to the Sgcd-null mice and associated with microvascular dysfunction (Factor et al., *Circulation* 66: 342–354 (1982)). However, the skeletal muscle of the cardiomyopathic hamster is not as severely dystrophic as in the Sgcd-null mice. Recent genetic studies revealed expression of δ-sarcoglycan transcripts in some tissues of the BIO 14.6 hamster (Sakamoto et al., *FEBS Letters* 447: 124–128 (1999)), indicating that the BIO 14.6 hamster may not be completely deficient in the δ-sarcoglycan protein. These observations indicate that the differences in severity of the clinical phenotypes are due to the difference in the type of the genetic lesion in each case.

These new animal models are useful in the identification of therapeutic compounds for the treatment of similar human conditions. Therefore, another aspect of the present invention is a method for identifying a therapeutic compound useful for treatment of an individual diagnosed with a deficiency in wild type β-sarcoglycan or δ-sarcoglycan. The deficiency may result from a efficiency in gene expression, or a deficiency in protein function. Such deficiencies include, without limitation, autosomal recessive limb-girdle muscular dystrophies of type 2F and type 2E. To identify therapeutic compounds for the treatment of a patient with a β-sarcoglycan deficiency, a mouse which is homozygous for a disrupted β-sarcoglycan gene is used. A candidate compound is administered to the mouse, and assays are performed to detect any therapeutic effects on the mouse which result from administration of the candidate compound. Therapeutic effects include, without limitation a reduction or reversal in disease progression, compared to the appropriate controls, and/or an alleviation of disease symptoms, compared to the appropriate controls. A candidate compound which produces such therapeutic effects upon administration to the mouse is to be considered a therapeutic compound for the treatment of an individual, usually a human, diagnosed with a β-sarcoglycan deficiency. To identify therapeutic compounds for the treatment of δ-sarcoglycan deficiency, a mouse which is homozygous for a disrupted δ-sarcoglycan gene is used in this method.

This method is useful for screening a variety of candidate compounds. Without limitation, candidate compounds include previously known drugs, small molecules (e.g. from a library), or genes for use in gene therapy. A candidate compound may also be any combination of these agents.

The method of administration of the candidate compound to the mouse will depend upon the properties of the candidate compound and any specific therapeutic effects which may be desired. For instance, because the lack of either δ-sarcoglycan or β-sarcoglycan expression in smooth muscle cells, especially vascular smooth muscle cells, contributes to cardiomyopathy, therapeutic effects regarding vascular disfunction are expected to be gained by administration of a therapeutic compound by means to contact the compound with smooth muscle cells, especially vascular smooth muscle cells, of the mouse In addition, administration by means to contact a therapeutic compound with skeletal muscle cells, or cardiac muscle cells, of the mouse is also expected to have therapeutic effects, since the genetic deficiency directly effects these tissues as well. Such administration may be achieved, without limitation by either intravenous, intraperitoneal, intramuscular, oral, or topical administration. The determination of the appropriate mode of administration of a candidate compound is within the ability of one of skill in the art through no more than routine experimentation.

Under circumstances where the candidate compound is a gene, the gene is to be administered under conditions appropriate for the expression of the gene in cells of the mouse. One such way it to incorporate the gene into a mammalian expression vector and deliver the expression vectors into target cells (e.g. smooth muscle cells, skeletal muscle cells, cardiac muscle cells) of the mouse. Some expression vectors promote integration of the gene into the genome of the target cells, other expression vectors remain separate from the cellular genome. Several potential expression vectors for use in this method are described above.

Cells of the Sgcd- or Sgcb-null mice may be obtained from the mice and propagated in culture for use in the identification of therapeutic compounds for the treatment of an individual with a respective non-dominant δ-sarcoglycan or β-sarcoglycan deficiency, respectively. Particularly useful cells to use in such a method are smooth muscle cells, especially vascular smooth muscle cells, and also skeletal muscle cells of the mouse. In the method, a candidate therapeutic compound is administered to the cells and then the cells are assayed for therapeutic effects which result from this administration. Determination of therapeutic effects depends upon the pathology of the specific cells used. For example, a partial or complete restoration of the dystroglycan complex may be used to indicate therapeutic effects in skeletal or cardiac muscle cells. Along the same lines, partial or complete restoration of the sarcoglycan-sarcospan complex, or an increase in the amount of α-, ε-sarcoglycan, sarcospan, and/or α-dystroglycan compared to control cells may be used to indicate therapeutic effects on smooth muscle cells.

Another aspect of the present invention relates to the treatment of ischemic heart disease which is caused by, or associated with, reduced expression of the sarcoglycan-sarcospan complex in vascular smooth muscle cells of an individual. Such a reduction in expression may be due to a defect in one or both δ-sarcoglycan genes of the individual, or to a defect in one or both β-sarcoglycan genes of the individual. One of skill in the art will recognize that other defects can also produce this phenotype in an individual. The method comprises contacting the vascular smooth muscle cells of the individual with a vascular smooth muscle relaxant. Experiments detailed in the Exemplification section below show that administration of the vascular smooth muscle relaxant, Nicorandil to Sgcd-null mice, prior to the application of physical stress, prevented mortality and the development of multiple myocardial lesions in treadmill stressed Sgcd-null mice. This strongly indicates that administration of a vascular smooth muscle relaxant (e.g. Nicorandil, Verapamil, Nitroglycerine, Dipyridmole) to an individual with reduced expression of the sarcoglycan-sarcospan complex in vascular smooth muscle cells will produce similar therapeutic results. Substantial therapeutic benefit can be obtained when administration precedes the onset of physical stress of the individual. Acceptable modes of administration include, without limitation, intraperitoneal, intravenous, subcutaneous, and oral administration. According to pharmacological studies, dilation of coronary artery microvessels depends on potassium channel activation and is mainly observed at low concentrations of Nicorandil (Kaski, J. C., *Cardiovasc. Drugs Ther.* 9: 221–227 (1992)). Therefore, it is preferable that the smooth muscle relaxants are administered at dose which ensures predominant action on the coronary artery microvasculature, without significantly lowering blood pressure. The appropriate dosage and route of administration varies with the specific condition of each individual, and can be determined by the skilled practitioner through no more than routine experimentation.

Administration of a vascular smooth muscle relaxant, by the methods described above may also be used to prevent ischemic injury in skeletal and cardiac muscle of an individual which has reduced expression of the sarcoglycan-sarcospan complex in his vascular smooth muscle cells. This type of ischemic injury results from conditions such as mammalian autosomal recessive limb-girdle muscular dystrophy type 2E or 2F. This method is also expected to be of therapeutic benefit to an individual suffering from other such conditions which result in a similar reduction of expression of the sarcoglycan-sarcospan complex in cells of the individual. Increased benefit may be obtained when administration occurs prior to the experience of physical stress.

Another aspect of the present invention is a method for identifying a therapeutic compound for the treatment of ischemic heart disease in an individual caused by, or associated with, reduced expression of the sarcoglycan-sarcospan complex in the vascular smooth muscle cells of the individual. In the method, a candidate compound is administered to a mouse which has reduced expression of the sarcoglycan-sarcospan complex in the vascular smooth muscle cells (e.g. a Sgcd-null or Sgcb-null mouse). Administration is by means to contact the candidate compound with the vascular smooth muscle cells of the mouse, similar to that in the above described methods. The mouse is then assayed for therapeutic effects which arise in response to administration of the candidate compound. Therapeutic effects include, without limitation, a reduction or reversal in the accumulation of ischemic injury, and or a reduction of symptoms which arise from ischemic injury. Therapeutic effects are detected by comparison of the mouse condition to the condition of the appropriate control mice. A detection of therapeutic effects is an indication that the administered compound has therapeutic properties.

Another aspect of the present invention is a method for identifying a therapeutic compound for the prevention of ischemic injury in skeletal and cardiac muscle of an individual, wherein the injury is caused by or associated with reduced expression of the sarcoglycan-sarcospan complex in vascular smooth muscle cells of the individual. Similar to the above described methods, a mouse which has reduced expression of the sarcoglycan-sarcospan complex in its vascular smooth muscle cells (e.g. a Scgd-null or Scgb-null mouse) is used to screen candidate compounds. A candidate compounds is administered to the mouse by means to contact the vascular smooth muscle cells of the mouse, as describe above. The mouse is then assayed for a decrease in the ischemic injury in skeletal and cardiac muscle which accumulates, attributable to the administration of the compound, by comparison to the appropriate control mice. It may be of benefit to subject the mouse to stress (e.g. using treadmill exercise) to accelerate ischemic injury, to more rapidly detect injury prevention. The detection of therapeutic effects are an indication that the administered compound has protective properties. Administration is accomplished by the above described methods.

The molecular mechanism for the vascular dysfunctions observed in Sgcd-null mice and Sgcb-null mice remains to be determined. Recent biochemical evidence suggests the presence of at least three interconnected subcomplexes, dystrophin, dystroglycan and sarcoglycan within the DGC (Crosbie et al., *J. Cell Boil.* 145: 153–165 (1999)). The results indicate that the expression of each of these subcomplexes is a prerequisite for the functional structural membrane association of the DGC. It may be possible that the absence of the SG-SSPN complex leads to structural and/or conformational changes of the remaining components of the DGC, which may be related to the abnormal contraction and/or dilation of the vascular smooth muscle. Yet another possibility is that metabolic and signalling pathways are involved in the microvascular dysfunction. Elevated levels of intracellular calcium, disturbances of the nitric oxide synthase pathway as well as increased activity of protein kinase C have been implicated in increased contractility and/or spasm of the microvasculature.

EXEMPLIFICATION

Section I

DISRUPTION OF THE δ-SARCOGLYCAN GENE LEADS TO DISRUPTION OF THE SARCOGLYCAN-SARCOSPAN COMPLEX IN VASCULAR SMOOTH MUSCLE AND REVEALS A NOVEL MECHANISM IN THE PATHOGENESIS OF CARDIOMYOPATHY AND MUSCULAR DYSTROPHY

Generation of the Sgcd-null Mice

In order to create Sgcd-null mice, a targeting vector was designed to replace exon 2, which encodes 63 amino acids of the intracellular domain and the entire transmembrane domain (FIG. 1). Southern blot analysis was performed on 370 neomycin resistant ES colonies which had received the targeting vector to identify clones which had appropriately integrated the targeting vector DNA. DNA from the ES colonies was digested with EcoRI or BamHI/XhoI and probed with probe A (FIG. 1) and B (FIG. 1), respectively. Probe A was seen to hybridize with a new 8.8-kb fragment, which was generated by the correct replacement of exon 2 by the neo cassette, in addition to the 7-kb wild type fragment. Probe B was seen to hybridize with a 5-kb fragment which was produced by digestion of the XhoI site introduced by the correct placement of the neo cassette, in addition to the 7.5-kb wild type allele. This analysis revealed homologous recombination in 7 independent clones. Two of these heterozygous clones were then used to produce chimeric founder mice. Heterozygous mice from the F1 generation were crossed to obtain Sgcd-null mice and the offspring were tested for exon 2 deletion by Southern blot and PCR analysis. PCR analysis of tail DNA purified from wild type, heterozygous, and Sgcd-null mice produced a 600 bp band corresponding to the wild type allele, and a 700 bp band corresponding to the null allele. The number of homozygous mutant offspring obtained was the expected 25%, based on Mendelian inheritance. Northern blot analysis, using the complete cDNA coding sequence of δ-sarcoglycan gene as a probe, revealed a transcript of 9-kb in the skeletal muscle of wild type, heterozygous, and homozygous Sgcd-null mice. An additional hybridization with a probe specific for exon 2 identified the 9-kb transcript only in the wild type and heterozygous, but not in the mutant mice, indicating a deletion of exon 2 from both alleles of the mutant mice. RT-PCR analysis performed with a forward primer in exon 1 and a reverse primer in exon 5, revealed a PCR product representing the normal transcript (600 bp) in wild type and heterozygous mice and an additional PCR product (400 bp) in heterozygous and mutant mice. Sequencing of this PCR product suggested that alternative splicing occurred between exon 1 and exon 3 of the δ-sarcoglycan gene. In this case, an open reading frame from exon 3 to exon 8 would be maintained. Translation of this smaller transcript would produce a 218 aa protein, lacking the entire transmembrane domain and part of the N-terminus. However, no protein was detected in the skeletal and cardiac muscle fibers of the Sgcd-null mice by western blot of total homogenates and KCl washed microsomes by using an affinity purified polyclonal antibody directed against the C-terminal or N-terminal portion of δ-sarcoglycan. Immunohistochemical analysis of skeletal and cardiac muscle revealed a complete absence of δ-sarcoglycan with the concomitant loss of the SG-SSPN complex. Overall, the Sgcd-null mice were fertile and females able to bear at least two litters. Preliminary data indicated an increased number spontaneous deaths in Sgcd-null mouse colony at around 6 months of age. Two founder mice were produced and analyzed, both of which exhibited the same phenotypes.

Sqcd-null Mice Exhibit a Severe Muscular Dystrophy

In order to examine the effect of targeted disruption of the δ-sarcoglycan gene on skeletal muscle morphology, hematoxylin and eosin (H&E)-stained sections of the calf, thigh, and diaphragm muscles were evaluated in wild type (n=8), Sgca-, Sgcd-heterozygous (n=26) and Sgcd-null mice (n=26) between the ages of 2 weeks and 6 months. Sgcd-heterozygous mice did not show any morphological abnormalities. Interestingly, the skeletal muscle of the Sgcd-null mice, even in the very young animals (n=8), showed extensive pathological alterations. The predominant feature was consistent with various stages of skeletal muscle necrosis or regeneration similar to pathological alterations observed in tissue infarcts. Severe dystrophic changes were evident in skeletal muscle at all three sites from a very early age (1 month). Areas of tissue regeneration had a large percentage of myocytes with centrally placed nuclei. Regions of full thickness necrosis or regeneration were seen in the diaphragms of these mice. Chronic dystrophic changes accumulated with age in all of these same muscle groups. Large regions of necrosis/regeneration were observed in calf and thigh muscles of mice at all ages. Severe necrotic lesions including central nucleation, endomysial fibrosis, atrophy, hypertrophy, and fatty infiltration were predominantly seen in the diaphragm in younger animals at 1 month of age. Similar findings were observed in a second founder from another cell line of targeted ES cells. Based on the evaluation of 200–1,100 myofibers per muscle, 80–100% of non-regenerating myocytes contained internally placed nuclei by the age of 1 month (n=4). In addition to the described severe necrotic/regenerative lesions, a broad spectrum of other dystrophic changes were observed in older (>4 months) Sgcd-deficient muscle (n=18). These changes included endomysial fibrosis, fiber splitting, hypertrophy, dystrophic calcification and fatty infiltration. Evaluation of creatine kinase (CK) levels in Sgcd-null mice revealed a 15–20-fold elevation of CK as compared to wild type mice.

Sqcd-null Mice Display Severe Cardiomyopathy

In order to evaluate whether disruption of the δ-sarcoglycan gene may cause cardiac abnormalities, H&E staining of transverse sections of hearts from wild type (n=8) and Sgcd-null mice between the ages of 2 weeks and 6 months (n=26) was performed. From 2 weeks to 3 months of age (n=8), hearts from Sgcd-null mice were nearly normal and only rare, small foci of necrosis were seen. Myocardial tissue studied after 3 months of age revealed more extensive alterations (n=18). Larger and more numerous foci of active cellular necrosis and granular calcium deposits involving small groups of myocytes were present. These foci were sharply demarcated from surrounding tissue, which appeared to be normal The localization and extent of pathology predilection sites varied considerably from animal to animal. In some hearts subendocardial regions were predominantly affected, whereas in others, pathological changes in the outer two-thirds of the free walls of both ventricles were observed. In older animals (5–6 months) [n=14] active myocardial necrosis was less evident, but various stages of calcification and fibrosis were observed. Interestingly, female mice that had been pregnant at least once (n=4) displayed more widespread and advanced cardiac alterations than age-matched virgin females (n=4). In contrast, extensive histopathological evaluations of the myocardium of Sgca-null mice (including pregnant females) showed no pathological alterations besides minimal calcification in some of the older animals. No coronary vessel histopathology at the light microscopy level was observed Disruption of the SG-SSPN Complex in the Smooth Muscle of the Coronary Arteries in Sqcd-null Mice The characteristic histopathological abnormalities suggested that alterations in vascular smooth muscle might be responsible for these findings. Recent biochemical studies (Straub et al., *J. Biol. Chem.*, in press (1999)) suggest that the composition of SG-SSPN complex in smooth muscle is distinct from that in skeletal and cardiac muscle. Consequently, immunohistochemical analysis was performed on components of the DGC in cardiac muscle fibers and smooth muscle cells of coronary arteries from wild type, Sgca- and Sgcd-null mice. In wild type mice, α-, β-, γ-, δ-, and ε-sarcoglycan, sarcospan and β-dystroglycan were homogeneously expressed at the cardiac muscle fiber membranes. β-, δ- and ε-sarcoglycan, sarcospan and β-dystroglycan were also strongly expressed in the smooth muscle cells of the coronary arteries. In contrast, α- and γ-sarcoglycan were not expressed in smooth muscle cells of coronary arteries. In cardiac muscle fibers of Sgca-null mice, α-sarcoglycan was absent from the sarcolemma, whereas δ-sarcoglycan was absent from the sarcolemma of Sgcd-null mice respectively. In addition, there was a concomitant loss of α-, β-, γ- and δ-sarcoglycan. Sarcospan was absent from the sarcolemma of both animal models. Interestingly, ε-sarcoglycan was absent from the sarcolemma of Sgcd-null mice in contrast to wild type and Sgca-null mice. However, the most remarkable difference between the Sgca- and the Sgcd-null mice was observed in the expression of the SG-SSPN complex in the smooth muscle of coronary arteries. While β-, δ-, and ε-sarcoglycan along with sarcospan were still strongly expressed in the coronary arteries of the Sgca-null mice, these proteins were completely absent in the smooth muscle cells of Sgcd-null mice. The same expression pattern was observed in smooth muscle cells of other blood vessels (e.g. the femoral artery). Staining with an antibody against smooth muscle actin confirmed the presence of smooth muscle in the vasculature. Western blot analysis of aortic tissue confirmed the immunohistochemical observation that the SG-SSPN complex is disrupted in Sgcd-null mice, while it is still preserved in aorta from wild type and Sgca-null mice. All analyses of knockout mice were compared to wild type controls. Taken together, these results indicate that targeted ablation of the δ-sarcoglycan gene leads to disruption of the SG-SSPN complex in smooth muscle, whereas the complex is preserved in smooth muscle cells of Sgca-null mice.

Coronary Artery Vascular Irregularities in Sqcd-null Mice

The Microfil® perfusion technique was used in vivo in order to determine whether disruption of the SG-SSPN complex in smooth muscle of coronary arteries indeed leads to vascular perfusion abnormalities. Wild type, Sgca-null and Sgcd-null mice at the age of 2–6 months were perfused, and cleared sections of the heart were visualized using trans-illumination with low-power magnification. The coronary microvessels were distributed normally and were smoothly tapered in both wild type and Sgca-null mice. Some animals showed areas of focal vessel narrowing but never showed any severe irregularities. In contrast, Sgcd-null mice displayed numerous areas of pronounced constrictions. Pre- and poststenotic dilation as an appearance of microaneurysm was frequently associated with these constrictions. Extensive areas of focal vascular lumen narrowing and a generalized sparseness of perfusion were observed. Interestingly, although general perfusion was diminished in capillaries of Sgcd-null mice, no constrictions were observed. Quantification of vascular abnormalities in Sgcd-null mice at different ages were determined by calculating the mean numbers of abnormal vessels ± SEM in 10 nonadjacent microscopic fields at a magnification of 10×. No lesions were detected in Sgca-null and wild type mice. Analysis of Sgcd-null mice revealed irregularities in 2 (5±1.1), 4 (11±1.5) and 6 months old mice (4±0.9) [n=10, in each age group respectively]. However, the most severe and abundant abnormalities were observed at the age of 4 months, a time when acute necrosis was first observed in Sgcd-null mice.

These results indicate that the disturbance of the vasculature precedes the onset of myocardial ischemic lesions.

The Microfil® in vivo perfusion enabled the study of long segments of coronary artery branches in three dimensions. Quantification of perfusion abnormalities in Sgcd-null mice revealed that vessel irregularities were present even in young mice at a stage without any overt signs of cardiac muscle necrosis. Moreover, the most severe and abundant perfusion abnormalities were observed at the time of acute ongoing necrosis, indicating that a certain degree of vascular dysfunction may be required to reach an ischemic threshold necessary to induce myocardial necrosis. These data indicate that the lesions observed in Sgcd-null mice are not an induced epiphenomenon caused by alterations of the cardiac muscle per se. Rather, the data indicate that increased vascular tone comprises blood supply in a diffuse manner leading to focal ischemic injury, necrosis and fibrotic changes.

Treadmill Exercise Initiates the Development of Cardiac Muscle Necrosis in Young Sgcd-null Mice In order to test the hypothesis that the observed abnormalities of the vasculature represent a dynamic hyperreactivity of the vasculature, which may be triggered by stress, wild type (n=20), Sgca- (n=20) and Sgcd-null mice (n=42) were exercised for 40 min using a treadmill. Treadmill exercise is one of the primary methods used clinically to induce cardiovascular stress in human and animals (Fewell et al., *Am. J. Physiol.* 273: H1595–H1605 (1997)) and is used to detect cardiovascular abnormalities (e.g. coronary artery dysfunction) that may not be readily apparent at rest. The exercised mice were studied at the age of 2–3 months a time where Sgcd-null mice do not show any overt signs of cardiac muscle necrosis, but do have microvessel abnormalities as revealed by perfusion studies. All mice were injected with Evans blue dye (EBD) 8 hr before the exercise. EBD is a small molecular mass tracer that tightly complexes with serum albumin. Normally, this is a membrane impermeable molecule, but if the sarcolemma integrity is compromised this dye readily penetrates into the cytoplasm of muscle fibers (Matsuda et al., *J. Biochem.* (Tokyo) 118: 959–964 (1995); Straub et al.,*J. Cell Biol.* 139: 375–385 (1997)). EBD uptake as well as routine histopathology was examined in the cardiac muscle. Interestingly, approximately ⅓ of the Sgcd-null mice died suddenly during the exercise while no death occurred in Sgca-null and wild type mice. The surviving Sgcd-null mice were sacrificed 36–48 hr after exercise for histological assessment of cardiac muscle.

All mice displayed multiple areas of EBD uptake corresponding to acute histopathological features of necrosis as revealed by H&E staining. Histological analysis of these myocardial lesions displayed coagulation necrosis, which is a characteristic histological feature observed in conditions associated with myocardial ischemia. No signs of EBD uptake from necrosis were detected in age matched nonexercised Sgcd-null or wild type mice. Only a few single necrotic cells were observed in Sgca-null mice. Quantification of Evans blue staining after treadmill exercise revealed 13–27% positive stained areas in cardiac muscle sections of Sgcd-null mice and less than 3% positive stained areas in Sgca-null mice.

In order to demonstrate that these observations were related to vascular dysfunction, a vascular smooth muscle relaxant compound, Nicorandil, was administered to the Sgcd-null mice. Nicorandil has been shown to relax coronary vascular smooth muscle by activation of potassium channels resulting in hyperpolarization of the smooth muscle membrane as well as by increasing cyclic GMP levels (Kukovetz et al., *J. Cardiovasc. Pharmacol.* 20 (Suppl.3): S1–S7 (1992)). In addition, Nicorandil has been shown to prevent coronary artery vasospasms under a variety of conditions (Kaski, J. C., *Cardiovasc. Drugs Ther.* 9: 221–227 (1992))

Intraperitoneal administration of Nicorandil, a vascular smooth muscle relaxant, was able to prevent the development of multiple myocardial ischemic lesions in all Sgcd-null mice (n=20) studied. No EBD uptake was observed in cardiac muscle of 2 months old exercised Sgcd-null mice after intraperitoneal application of Nicorandil for 3 days prior to the exercise. Microfil® perfusion of coronary arteries in Sgcd-null mice after administration of Nicorandil revealed no evidence of vascular constrictions and displayed smoothly tapered branches of the coronary vascular bed. In addition, there was overall greater density of the vasculature. Nicorandil, at the dose given, did not lower the systemic blood pressure in Sgcd-null mice. No alteration of the general behavior during exercise or any cardiac muscle abnormalities was observed during or after exercise of wild type or Sgca-null mice after administration of Nicorandil. In addition, perfusion studies in Nicorandil treated Sgcd-null mice showed the coronary microvascular bed free of constrictions and focal luminal narrowing. The functional disturbance of the vasculature was demonstrated to initiate ischemic myocardial necrosis. As the mice aged, this damage developed into a severe cardiomyopathy.

Methods of the Invention, Section I

Isolation of mouse δ-SG qenomic and cDNA clones.

One RT-PCR product from mouse skeletal muscle RNA was obtained using the hamster primer HadFor5 (5'-AGCTCAGAGGGGCCACAC-3' (SEQ ID NO: 1), exon 2) and the mouse primer MdRev2 (5'-CAGCCAGTGTTTCAAGCCAA-3' (SEQ ID NO: 2), exon 8). This product, containing exons 2–8 of the δ-sarcoglycan gene, was used to screen a Stratagene 129/SV mouse genomic library in vector λFIXII (La Jolla, CA). Three positive clones were subcloned into pBlueScript KS (+) and restriction enzyme mapped using standard procedures.

Generation of Sgcd-null Mice.

The δ-SG targeting vector was constructed using the positive-negative selection vector pPNT. EcoRI and BamHI sites were introduced by high fidelity PCR mutagenesis (Takara enzyme) at the ends of a 6-kb fragment that contains part of the δ-SG intron 1 and exon 1b. The DNA was digested by EcoRI/BamHI and inserted in between the tk and neo genes of the vector. The second insert was obtained by subcloning a 5-kb NotI-EcoRI δ-SG intron 2 fragment into the digested NotI-EcoRI pBlueScript. The insert was isolated by NotI-XhoI digestion and cloned into the NotI and XhoI sites of the plasmid. 2992 bp were deleted from the genome of the recipient cell after homologous recombination, and replaced by the neo gene. This deletion included 2277 bp of intron 1, all of exon 2, and 576 bp of intron 2 of the δ-SG (FIG. 1). The construct introduced into the recipient cells contained 5 kb of intron 1 and 5 kb of intron 2, and lacked exon 2 of the δ-sarcoglycan gene, which was replaced with a neomycin resistance gene inserted between the two introns in the opposite transcriptional orientation as the δ-sarcoglycan exon which was replaced. R1 embryonic stem cells (ES) were grown and electroporated with 10 µg of the NotI linearized targeting plasmid. Colonies surviving G418 and Gancyclovir were isolated, expanded, and screened by Southern blot analysis for appropriate incorporation of the vector DNA. ES cell lines from two different, correctly targeted clones were injected into C57BL/6J blastocysts and transferred into pseudopregnant females. After germ-line transmission, DNA was extracted from the offspring's tails and the genotyping was done by PCR using the following three different primers in the same reaction: NeoTR (5'-GCTATCAGGACATAGCGT TGG CTA -3' (SEQ ID NO: 3); Mdint1F (5'-GCAAACTTGGAG AGTGAAGAGGC -3' (SEQ ID NO: 4); and Mdint1R (5'-GAGGCATATAAAGTTTGCACGAC -3' (SEQ ID NO: 5)).

Northern Blot Analysis.

Total RNA was isolated from wild type, δ-SG+/−, and δ-SG −/− skeletal muscle tissue using RNAzol B (Tel-Test) according to the manufacturer specifications. 20 µg of the RNA was subjected to electrophoresis on a 1.25% agarose gel containing 5% formaldehyde, blotted to Hybond membrane (Amersham), and hybridized with either a 760 bp exon 2–8 probe or an exon 2 probe from mouse δ-SG cDNA.

Histopathology studies.

Wild type mice (n=8), Sgca- (n=26), Sgcd-heterozygous (n=26) and Sgcd-null mice (n=26) were anaesthetized with pentobarbital (0.75 mg/10 g of body weight) via intraperitoneal injection. Subsequently, the animals were perfused with PBS (15 ml) followed by 15 ml of 10% buffered formalin fixative solution. After embedding the tissue in paraffin, hematoxylin and eosin (H&E) stained sections (4 µm) were prepared in order to characterize skeletal and cardiac muscle pathology. Some animals were sacrificed by cervical dislocation and H&E staining was performed on cryosections of skeletal and cardiac muscle. Furthermore, H&E sections of brain, lung, liver, kidney and spleen were performed in some animals. No histopathology was observed in these non-muscle tissues. Creatine kinase values were determined in blood serum from wild type and Sgcd-null mice using the creatine kinase assay kit from Sigma.

Immunofluorescence Analysis.

Hearts and skeletal muscle were isolated from wild type, Sgca- and Sgcd-null mice and rapidly frozen in liquid nitrogen cooled isopentane. 7 µm cryosections were prepared and analyzed by immunofluorescence using different antibodies as described previously (Duclos et al., *J. Cell Boil.* 142: 1461–1471 (1998)).

Antibodies.

Rabbit polyclonal antibodies against α-sarcoglycan (rabbit 98), dystrophin (rabbit 31), the laminin α2 chain, β-sarcoglycan (goat 26), and δ-sarcoglycan N- and C-terminal peptide (rabbit 214 and 229, respectively), α-dystroglycan fusion protein D (goat 20), and against β-dystroglycan C-terminal peptide (rabbit 83), sarcospan and ε-sarcoglycan (rabbit 235 and 232, respectively) were described previously (Duclos et al., *J. Cell Boil.* 142: 1461–1471 (1998)). An affinity purified rabbit polyclonal antibody was produced against a COOH-terminal fusion protein (aa 167–291) of γ-sarcoglycan. A commercially available mouse monoclonal antibody was used to detect smooth muscle actin (Sigma).

Microfil® Perfusion.

In order to study coronary microvascular perfusion mice were anesthetized with Phenobarbital 75 mg/kg body weight and a bilateral sternum incision was performed to expose the left atrium. 1–1.5 ml of Microfil®, a liquid silicon rubber (Flow tech, Carver, Massachusetts) was perfused into the left atrium. The heart continued beating for about 1 min and after contraction stopped the heart was rapidly excised and cured on ice for about 10 min. Adequacy of vascular perfusion was judged by the white blush that developed in the myocardium as well as the white filling of other main arteries (mesenteric artery and femoral artery) of the mouse body. The heart was fixed in 10% formalin for 24 hr and the next day the tissue was sliced into 2 mm thick transverse cross sections and cleared by sequential 24-h immersions in 25, 50, 75, 95 and finally 100% ethyl alcohol. On day 6, specimens were placed in pure methyl salicate for 12–24 hr. Microvascular perfusion was visualized with both epi- and tans-illumination and examined under low power magnification (×10–20). the vascular irregularities in Sgcd-null mice at different ages (2, 4, and 6 months) were quantified by counting the number of abnormal individual vessel segments in 10 nonadjacent microscopic field using a low magnification (10×) and the mean number of abnormal vessels were calculated for each mouse. An average number of abnormal vessels ± SEM were then calculated for each age group. Vessels segments with more than one abnormality were only counted once.

Treadmill Exercise.

Animals were exercised using the Omnipacer Treadmill Model LC4/M-MGA/AT, Accuscan Instruments, Inc., which had an adjustable belt speed (0–100 m/min), shock bars with adjustable amperage and an on-and-off shock switch for each lane. Animals were exercised at 12–17 m/min for about 10 min and for 25–30 m/min for the remaining 50 min. If an animal became exhausted, the shock bar of this lane was turned off and the animal was allowed to rest at the back of the treadmill for a short period of time. Wild type (n=20), Sgca- (n=20) and Sgcd-null mice (n=42) were divided in approximately equal numbers of male and females. All mice were injected with Evans blue dye (0.5 mg EBD/0.05 ml PBS) intraperitoneally 8 hr before the exercise. Animals were injected with 50 μl of this solution per 10-g body weight. All surviving animals were kept alive for 36–48 hr and serial sections of cardiac muscle were studied for Evans blue uptake and for histopathological signs of necrosis by using routine H&E technique. The effect of Nicorandil treatment on treadmill performance in wild type (n=6), Sgca- (n=6) and Sgcd-null mice (n=20) was studied after 3 days of intraperitoneal injection of Nicorandil at a dose of 1 mg/kg body weight twice a day. Quantification of Evans blue positive stained areas in sections of cardiac muscle from Sgca- and Sgcd-null mice (n=20, each group) was done by using the Scion image program. The percentage of positive stained areas was calculated by dividing the area of staining by the total area of the analyzed heart section.

SECTION II

DISRUPTION OF THE β-SARCOGLYCAN GENE

Generation of Sqcb-null Mice

Figure 2:
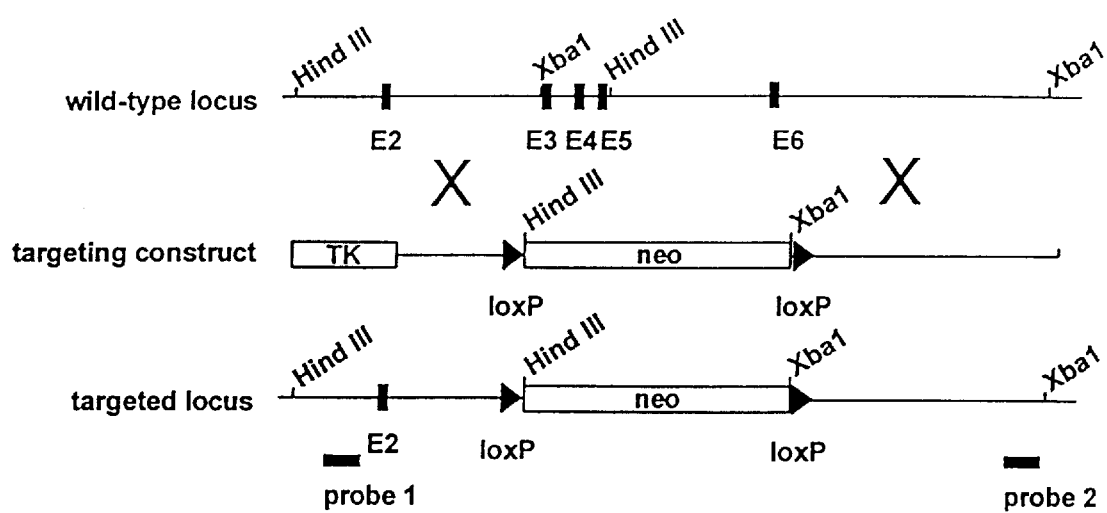
FIG. 2 is a schematic representation of targeted disruption of the mouse Sgcb-null mutant mice. Shown is a restriction map of the wild-type Sgcb allele (top), the targeting vector (middle), and the predicted targeted allele following homologous recombination (bottom). Exons 3, 4, 5 and 6 were replaced by phosphoglycerate kinase neomycin cassette (neo). The position of the neo and tk cassettes, hybridization sites of probes 1 and 2, for Northern and Southern analyses, are also indicated.

A P1-clone containing the mouse β-sarcoglycan gene was characterized in order to design a targeting vector for the generation of Sgcb-null mice. Murine and human β-sarcoglycan are highly homologous at the amino acid level and the structural organization of the gene into six exons is shared by both species (GenBank/EMBL/DDBJ accession number AF169288). Given that most human mutations have been found in exons 3, 4, 5 and 6, which encode part of the transmembrane domain and the extracellular portion of β-sarcoglycan (Bönnemann et al., *Nat. Genet.* 11: 266–273 (1995); Lim et al., *Nat. Genet.* 11: 257–265 (1995); Bönnemann et al., *Hum. Mol. Gen.* 5: 1953–1961 (1996); Bönnemann et al., *Neuromusc. Disord.* 8: 193–197 (1998); Duclos et al., *Neuromusc. Disord.* 8: 30–38 (1998)), exons 3, 4, 5 and 6 were targeted to create a mutant allele of Sgcb representative of human mutations. Homologous recombination replaced exons 3 through 6 with the phosphoglycerate kinase promotor/neomycin phosphotransferase CDNA (FIG. 2). A total of 361 colonies of ES cells surviving G418 and gancyclovir selection were analyzed by Southern blotting for the presence of homologous recombination. DNA from the ES cells was prepared and digested with Hind III or Xba 1 and probed by Southern blot with probe 1 (see FIG. 2) and 2 (see FIG. 2) respectively. The correct replacement of exons 3–6 by the neo cassette of the targeting construct produced a new 3.9 kb Hind III fragment, in addition to the 7.4 kb wild type Hind III fragment, which was identified with probe 1. 15 correctly targeted clones were identified. Three of these clones were used to produce chimeras for germline transmission. Southern blot analysis of tail DNA from the heterozygous and homozygous progeny produced revealed the same bands as seen in the ES cells, confirming the disruption of the β-sarcoglycan gene. Heterozygous mice appeared normal and homozygous mice were produced in expected numbers in accordance with Mendelian inheritance. The effect of the mutation on β-sarcoglycan RNA was assessed by Northern blot analysis. A cDNA probe specific for exon 2 (probe 1, FIG. 2) was used to probe RNA extracted from skeletal muscle of wild-type, heterozygous, and Sgcb-null mice. This probe detected the previously described β-sarcoglycan transcripts of 4.4, 3.0, and 1.4 kb in both wild-type and heterozygous mice. In contrast, none of the known transcripts were detected in Sgcb-null mice. A faint transcript of 4 kb, however, was detected in Sgcb-null mice. This transcript may represent a transcript containing exons 1 and 2 and the neo-cassette, however, attempts to amplify such a transcript with RT-PCR have been unsuccessful. A cDNA probe specific for exon 6 (probe 2, FIG. 2) did not detect any β-sarcoglycan transcripts in the Sgcb-null animals, but did detect the expected bands in wild-type and heterozygous animals.

Western blot and immunofluorescence analysis were also performed on progeny mice to analyze β-sarcoglycan protein expression. Monoclonal and polyclonal antibodies specific for the N-terminus of β-sarcoglycan (epitopes between amino acids 1–65, encoded from exon 1 and parts of exon 2) were used to probe membrane-enriched preparations of skeletal, cardiac and lung membranes of wild-type, heterozygous, and Sgcb-null mice, by Western blot analysis. The analysis detected β-sarcoglycan protein in wild-type and heterozygous mice, but not in Sgcb-null mice. Immunofluorescence analysis detected β-sarcoglycan at the sarcolemma in wild-type skeletal and smooth muscle, but not at the sarcolemma of skeletal or smooth muscle of Sgcb-null mice. Two founder mice were produced and analyzed, both of which exhibited the same phenotypes.

Sqcb-null Mice Develop a Severe Muscular Dystrophy and Cardiomyopathy

To evaluate the consequences of β-sarcoglycan deficiency, hematoxylin and eosin (H&E)-stained sections of the calf, thigh and diaphragm muscle in wild type, heterozygous and Sgcb-null mice were examined. Histopathological features of muscular dystrophy were never observed in wild-type or heterozygous animals. In Sgcb-null mice, however, pronounced morphological changes were detected. Severe dystrophic changes were observed in the Sgcb-null mice. Large areas of necrosis were observed in calf, thigh and diaphragm muscles of mice at all ages. Other dystrophic changes included internally placed nuclei of non-regenerating fibers (based on the evaluation of 200–1, 100 myofibers per muscle, 80–100% of non-regenerating myocytes contained internally placed nuclei at the age of 2 months), fiber splitting and hypertrophy, extensive dystrophic calcification, endomysial fibrosis and massive fatty infiltration. Sgca-null mice have previously been generated (Duclos et al., *J. Cell Boil.* 142: 1461–1471 (1998)) and it is interesting to note that upon comparison, the skeletal muscle pathology was much more severe in Sgcb-null mice. For example, large areas of necrosis and fatty infiltration were not detected in Sgca-null mice.

Consistent with the severe dystrophic pattern, 13–16-wk-old Sgcb-null mice displayed elevated serum creatine kinase activity compared to age-matched wild-type and heterozygous mice. EBD injections into 9-wk-old Sgcb-null mice revealed uptake of the blue dye in various skeletal muscles, indicating compromised sarcolemma integrity, whereas no EBD staining was seen in control mice.

Dystrophin defects, including Duchenne or Becker muscular dystrophies, are also manifested at the cardiac level (Towbin, J. A., *Curr. Opin. Cell Biol.* 10: 131–139 (1998)). Less is known about the heart involvement in muscular dystrophies caused by sarcoglycan mutations. To evaluate the consequences of β-sarcoglycan deficiency in the heart H&E stainings of transverse sections of hearts from wild-type, heterozygous and Sgcb-null mice was performed. No cardiac abnormalities were observed in control mice of any age. In sharp contrast, small necrotic areas already in 9-wk-old hearts from Sgcb-null mice were detected. Similar histological analysis of hearts of 20-wk-old Sgcb-null animals revealed more extensive alterations. Prominent necrotic areas, resembling ischemic-like lesions, were present throughout the right and left ventricle. In 30-wk-old animals, active myocardial necrosis was less evident and instead widespread areas of fibrosis were detected.

β-Sarcoglycan-Deficiency Causes Loss of the Sarcoglycan-Sarcospan Complex, the Dystroglycan Complex and ε-Sarcoglycan in Skeletal, Cardiac and Smooth muscle Immunofluorescence analysis for each component of the DGC was performed in order to analyze the consequences of a β-sarcoglycan deficiency in skeletal, cardiac and smooth muscle at the molecular level Skeletal muscle cryosections from wild-type and Sgcb-null mice (4 week old) were stained independently with antibodies against α-sarcoglycan, β-sarcoglycan, γ-sarcoglycan, δ-sarcoglycan, ε-sarcoglycan, sarcospan, dystrophin, α-dystroglycan, β-dystroglycan, and laminin α2 chain. Immunofluorescence analysis revealed that β-sarcoglycan was absent from the sarcolemma of skeletal muscle fibers in Sgcb-null mice. Also, α-, γ-, and δ-sarcoglycan were concomitantly reduced along with sarcospan. Interestingly, ε-sarcoglycan was also reduced at the sarcolemma. Dystrophin staining appeared normal in Sgcb-null mice. α- and β-dystroglycan appeared slightly reduced whereas the laminin α2 chain was present at comparable levels with control skeletal muscle. Similar results were also obtained in heart To evaluate if the absence of β-sarcoglycan also affected the expression of the other sarcoglycans and sarcospan in smooth muscle, immunofluorescence analysis was performed on lung smooth muscle. Lung cryosections from wild-type and Sgcb-null mice (4 week old) were stained independently with antibodies against α-, β-, γ-, δ-, and ε-sarcoglycan, and also sarcospan. This analysis revealed that β-, δ- and ε-sarcoglycan and sarcospan were all expressed in lung smooth muscle of pulmonary arteries in wild-type mice whereas α- and γ-sarcoglycan were not detected. Absence of β-sarcoglycan in vascular smooth muscle also affected the expression of the smooth muscle sarcoglycans along with sarcospan, which was concomitantly greatly reduced.

To further examine the expression of DGC components, immunoblot analysis was performed on isolated membrane preparations from wild-type, heterozygous and homozygous mutant skeletal, cardiac and smooth muscle. Skeletal, cardiac and lung KCl-washed microsomes from wild-type, heterozygous and Sgcb-null mice were analyzed by 3–12% SDS-PAGE and immunoblotted with antibodies against the sarcoglycans (α-, β-, γ-, δ-, and ε-), sarcospan, dystrophin, and α-dystroglycan. Blots were also probed with antibodies against the α2 subunit of the dihydropyridine receptor to verify equal loading of protein samples.

In accordance with the immunofluorescence analysis, β-sarcoglycan was determined to be absent in skeletal and cardiac muscle of Sgcb-null mice by Western blot analysis. Heterozygous mice expressed levels of β-sarcoglycan similar to the wild type control. Furthermore, α-, γ-, and δ-sarcoglycan were concomitantly reduced in both skeletal and cardiac muscle from Sgcb-null mice. Lung tissue was used as a source for smooth muscle. As expected, β-sarcoglycan was deficient in lung of Sgcb-null mice. As noted above, α-sarcoglycan is not expressed in smooth muscle.

Although, as discussed above, δ-sarcoglycan was not detected in any cell-type in the lung by immunofluorescence, δ-sarcoglycan was detected by Western blot analysis of wild-type and heterozygous lung tissue. This same analysis indicated that γ-sarcoglycan expression was greatly reduced in Sgcb-null lung tissue. In addition, δ-sarcoglycan levels were significantly reduced in smooth muscle of Sgcb-null mice. Furthermore, ε-sarcoglycan and sarcospan levels were greatly reduced in the three muscle lineages of Sgcb-null mice.

In agreement with the immunofluorescence analysis, α-dystroglycan levels were determined to be greatly reduced in skeletal muscle of Sgcb-null mice, but Western blot analysis. In the supernatant from Sgcb-deficient skeletal muscle membrane preparations, α-dystroglycan was enriched and fully glycosylated, but obviously failed to be stably anchored to the membrane without the sarcoglycans. In cardiac muscle of Sgcb-null mice, α-dystroglycan was moderately reduced. Dystrophin was moderately reduced in skeletal muscle of Sgcb-null mice, not altered in cardiac muscle, but greatly reduced in smooth muscle.

Vascular Irregularities in Sqcb-null Mice

The above observations indicate that a deficiency of β-sarcoglycan in vascular smooth muscle leads to a loss of the sarcoglycan-sarcospan complex in smooth muscle. The predominant characteristic feature of the muscular dystrophy and cardiomyopathy was focal areas of necrosis, resembling the pathological observations seen in tissue infarcts, occurring in ischemic injury. Therefore, loss of the smooth muscle complex in the vasculature and the presence of necrotic areas prompted investigation into whether the presence of abnormalities in the vasculature contributed to the pathological changes of skeletal and cardiac muscle. The Microfil® perfusion technique was used in vivo to study the organization of various vascular beds in skeletal and cardiac muscle of the mutant mice. Wild-type and Sgcb-null mice of 4 weeks of age were perfused and cleared sections of the diaphragm and heart were analyzed using trans-illuminations with low-power magnification Interestingly, Sgcb-null mice exhibited numerous areas of vascular constrictions often associated with pre- and poststenotic aneurysm in the vasculature of both diaphragm and heart, which was never detected in wild-type mice. In addition, the vessels of Sgcb-null mice exhibited a serrated contour rather than smoothly tapered vessel walls that are seen in wild-type mice. Functional disturbance of the coronary artery microvasculature was detected at an age of 4 weeks, before any overt signs of cardiac morphological alterations were observed. Similarly, vascular irregularities in the diaphragm were observed in 4-wk-old Sgcb-null mice, at a time when acute necrosis starts to occur in the skeletal muscle. These observations indicate that the disturbance of the vasculature precedes the onset of ischemic-like lesions in Sgcb-null mice.

Presence of a Distinct ε-Sarcoglycan Complex in Skeletal Muscle

Although ε-sarcoglycan is expressed in skeletal muscle (Ettinger et al., 1997; McNally et al., 1998) there are no reports of ε-sarcoglycan being associated with the skeletal muscle sarcoglycans. In the membrane preparations of Sgcb-null mice, ε-sarcoglycan was observed to be greatly reduced, suggesting that ε-sarcoglycan could be part of a skeletal muscle sarcoglycan complex. To test this hypothesis DGC was isolated from skeletal muscle of wild-type mice, Sgca-null and Sgcb-null mice. The skeletal muscle DGC was extracted by digitonin and further purified by WGA affinity chromatography followed by centrifugation of the skeletal muscle DGC through sucrose gradients. The migration of the DGC complex during high-speed centrifugation through sucrose gradients has previously been demonstrated (Crosbie et al., FEBS Lett. 427: 270–282 (1998)). Proteins from the sucrose gradient fractions were separated by SDS-PAGE using 3–12% polyacrylamide gels. Nitrocellulose transfers of identical samples were probed with antibodies against the α-, β-, and γ-sarcoglycans, and α- and β-dystroglycan. α-, β-, γ- and δ-sarcoglycan were observed to migrate in fractions 7–9 in wild-type mice. Western blotting of the same fractions with antibodies against ε-sarcoglycan demonstrated that ε-sarcoglycan co-migrated in the same fractions as the other sarcoglycans along with α- and β-dystroglycan, although a peak of α-dystroglycan was also seen in earlier fractions. In the Sgca-null mice (deficient in α-sarcoglycan) α-sarcoglycan was absent, and β-sarcoglycan was greatly reduced. Some γ- and δ-sarcoglycan remained but peaked in earlier fractions (5–7 instead of 7–9). ε-sarcoglycan, however, remained in fractions 7–9. In contrast, α-dystroglycan was absent in fractions 7–9, but was still present in the earlier fractions. β-dystroglycan was also absent from fractions 7–9, but some β-dystroglycan was still present in fractions 4–6, although the remaining β-dystroglycan was not associated with the remaining α-dystroglycan or the remaining γ-sarcoglycan. Together, these results indicate that deficiency of α-sarcoglycan causes dissociation of the sarcoglycan and dystroglycan complexes, without affecting the presence of ε-sarcoglycan. This is in contrast to DGC preparations from Sgcb-null mice in which ε-sarcoglycan was greatly reduced. Moreover, in Sgca-null mice, some γ- and δ-sarcoglycan remained. In DGC preparations from Sgcb-null mice, however, all the sarcoglycans were observed to be absent. Also, α-dystroglycan was absent from fractions 7–9, but remained in the earlier fractions. Some β-dystroglycan also remained in Sgcb-null mice. In summary, loss of β-sarcoglycan causes dissociation of the sarcoglycan and dystroglycan complex and also of ε-sarcoglycan whereas mice deficient for α-sarcoglycan show normal e-sarcoglycan expression. These data indicate the presence of a ε-sarcoglycan containing complex in skeletal muscle. However, it is not associated with the tetrameric unit of α-, β-, γ- and δ-sarcoglycan, since this complex is very much reduced in Sgca-null mice, and ε-sarcoglycan is retained in these mice. Nevertheless, the expression of ε-sarcoglycan is obviously affected by the β-sarcoglycan mutation, suggesting that β-sarcoglycan and ε-sarcoglycan may be associated.

Methods of the Invention, Section II

Construction of Targeting Vector.

Hind III fragments of a P1 clone containing the mouse β-sarcoglycan gene (obtained from Genome Systems, Inc.) were subcloned into pBluescript KS (+) (pBS) and analyzed using restriction mapping and sequencing (Genbank/EMBL/DDBJ accession number AF 169288). The long arm of homology in the targeting vector was a 7.2 kb Hind III fragment upstream of exon 6, which had been subcloned into pBS and cut with Xhol to generate a 6.5 kb fragment. The short arm was a 1.8 Kpnl fragment carrying approximately half of the intron between exons 2 and 3. These fragments were inserted into cloning sites of pPNT flanking a PGK-neomycin resistance cassette to produce a DNA construct which contained 1800 bp of intron 2 and 6500 bp of sequences which begin 498 directly downstream of exon 6, of the β-sarcoglycan gene. The neomycin resistance gene was located between the intron 2 sequences and the sequences downstream of exon 6. The vector included a thymidine kinase cassette distal to the short arm. The mutant gene therefore lacked - ~7.5 kb which included exons 3, 4, 5 and 6, and introns 3, 4, and 5.

Generation of Sqcb-Deficient Mice.

The targeting vector was linearized with Notl and transferred into 2×107 R1 ES cells by electroporation (240 V, 500 µF; Bio-Rad Gene Pulser; Hercules, Calif.). Clones surviving growth in G418 and Gancyclovir were isolated. Targeting fidelity was determined by Southern blot analysis. Correct targeting resulted in a deletion of a region of approximately 7.5 kb, which included 1606 bp of intron 2, the entire exon 3, 4, 5, 6, intron 3, 4, and 5, and also 498 bp immediately downstream of exon 6. The deleted region was replaced with the PGK-neomycin cassette.

Cells from three correctly targeted clones were microinjected into C57BL/6J blastocysts and transferred into pseudopregnant recipients. Chimeras from the three independently derived ES cells gave rise to heterozygous mice which in turn were mated to generate homozygous mutants that were genotyped using Southern blot analysis on DNA from tail biopsies. All animals were kept in the animal care unit of the University of Iowa College of Medicine according to the animal care guidelines.

Northern Blot Analysis.

Total RNA from control, heterozygous, and homozygous-null mutant skeletal muscle was extracted using RNAzol B (Tel-Test, Friendswood, Tex.) according to manufacturer specifications. 20 µg of total RNA was run on a 1.25% agarose gel containing 5% formaldehyde and transferred to Hybond N Membrane (Amersham Corp., Arlington Heights, Ill.). RNA was cross-linked to the membrane using a Stratagene UV cross-linker (La Jolla, Calif.). Membranes were then prehybridized and hybridized with either a 203 bp exon 2 specific probe (Probe 1, FIG. 2) or a 253 bp exon 6 specific probe (Probe 2, FIG. 2). Washes were carried out at 65° C. in 1×SSC/1% SDS initially, then 0.1×SSC/1% SDS. Blots were exposed for autoradiography.

Histopathology Studies

Wild type, heterozygous and Sgcb-null mice were anaesthetized with Metofane. Subsequently, the animals were perfused with 15 ml of PBS followed by 15 ml of 10% buffered formalin fixative solution. After embedding the tissue in paraffin, hematoxylin and eosin (H&E) stained sections (4 μm) were prepared to characterize skeletal and cardiac muscle pathology.

Evans Blue Dye Injection and Serum Creatine Kinase Analysis.

Evans blue dye (EBD) (Sigma Chemical Co., St. Louis, Mo.) was dissolved in PBS (10 mg/ml) and sterilized by passage through membrane filters with a pore size of 0.2 μm. Mice were anaesthetized with Metofane and injected in the retro-orbital sinus with 0.05 ml/10 g of body weight of the dye solution. Animals were sacrificed 4 hr after injection by cervical dislocation. Muscle sections for microscopic Evans blue detection were incubated in ice-cold acetone at −20° C. for 10 min, and after a rinse with PBS, sections were mounted in Vectashield mounting medium (Vector Laboratories, Inc., Burlingame, Calif.) and observed under a Zeiss Axioplan fluorescence microscope (Carl Zeiss, Inc., Thornwood, NY). Quantitative, kinetic determination of creatine kinase activity in serum of wild-type, heterozygous and Sgcb-null mice was measured using a Hitachi 917, on blood drawn from retro-orbital sinus.

Antibodies.

Monoclonal antibody IIH6 against α-dystroglycan (Ervasti and Campbell, 1991) was previously characterized. Monoclonal antibodies Ad1/20A6 against α-sarcoglycan, βSarc/5B1 against β-sarcoglycan, and 35DAG/21B5 against δ-sarcoglycan were generated in collaboration with L.V.B. Anderson (Newcastle General Hospital, Newcastle upon Tyne, UK). Monoclonal antibody 43DAG/8D5 against β-dystroglycan was generated by L. V. B. Anderson (Newcastle General Hospital, Newcastle upon Tyne, UK). Rabbit polyclonal antibodies against α-sarcoglycan (rabbit 98) (Roberds et al., *J. Biol. Chem.* 268: 23739–23742 (1993)), δ-sarcoglycan (rabbits 215 and 229) (Holt et al., *Mol. Cell* 1: 841–848 (1998)), ε-sarcoglycan (rabbit 232) (Duclos et al., *J. Cell Biol.* 142: 1461–1471 (1998); Duclos et al., *Neuromusc. Disord.* 8: 30–38 (1998)), sarcospan (rabbit 235) (Duclos et al., *J. Cell Boil.* 142: 1461–1471 (1998); Duclos et al., *Neuromusc. Disord.* 8: 30–38 (1998)), dystrophin (rabbit 31) (Ohlendieck et al., *J. Cell Biol.* 115: 1685–1694 (1991)), the α2 subunit of dihydropyridine receptor (rabbit 136) (Ohlendieck et al., *J. Cell Boil.* 115: 1685–1694 (1991)), and the laminin α2 chain (Allamand et al., *Hum. Mol. Gen.* 6: 747–752 (1997)) were described previously. The goat polyclonal antibody against β-sarcoglycan (goat 26) was also described previously (Duclos et al., *J. Cell Boil.* 142: 1461–1471 (1998); Duclos et al., *Neuromusc. Disord.* 8: 30–38 (1998)). An affinity purified rabbit polyclonal antibody (rabbit 245) was produced against a COOH-terminal fusion protein (amino acids 167–291) of δ-sarcoglycan. In addition, an affinity purified rabbit polyclonal antibody (rabbit 256) was produced against an $NH_2$-terminal fusion protein (amino acids 1–25) of sarcospan.

Microfil® Perfusion.

Wild-type and Sgcb-null mice were anesthetized with 75 mg/kg body weight Phenobarbital and a bilateral sternum incision was performed to expose the left atrium. 1 ml of Microfil®, a silicon rubber (Flow Tech., Carver, Mass.), was perfused into the left atrium. The heart continued beating for about 1 min and after contraction stopped, the heart and diaphragm were rapidly excised and cured on ice for about 10 min. Adequacy of vascular perfusion was judged by the white blush that developed in the ventricular wall as well as a white filling of other main arteries including the mesenteric artery and femoral artery. The hearts were fixed in 10% formalin for 48–72 hr and cardiac tissue was sectioned into 2 mm thick transverse cross sections. The diaphragms were taken out as whole tissue and were not further cut. The tissues were subsequently cleared by sequential 24 hr immersions in 25, 50, 75, 95 and finally 100% ethanol. On day 6, specimens were placed in pure methyl salicylate for 12–24 hr. All steps were done at room temperature. Microvascular perfusion was visualized with trans-illumination and examined under low power magnification.

Immunofluorescence Analysis.

For immunofluorescence analysis 7 μm transverse cryo-sections were prepared from wild-type, heterozygous and Sgcb-null mutant skeletal muscle, cardiac muscle, lung, bladder and esophagus. All following steps were performed at room temperature. Sections were blocked with 5% BSA in PBS for 20 min and then incubated with the primary antibodies for at least 90 min. After washing with PBS, sections were incubated with Cy3-conjugated secondary antibodies (1:200) for 1 hr and then washed in PBS. Subsequently, sections were mounted with Vectashield (Vector Laboratories, Inc., Burlingame, Calif.) mounting medium and observed under a Zeiss Axioplan fluorescence microscope (Carl Zeiss Inc.) or an MRC-600 laser scanning confocal microscope (Bio-Rad Laboratories, Hercules, Calif.).

Immunoblot Analysis of Membrane Preparations.

KCl-washed membranes from skeletal and cardiac muscle and lung were prepared as described previously (Ohlendieck et al., *J. Cell Biol.* 115: 1685–1694 (1991)) with the addition of two protease inhibitors, calpeptin and calpain inhibitor I (Duclos et al., *J. Cell Boil.* 142: 1461–1471 (1998); Duclos et al., *Neuromusc. Disord.* 8: 30–38 (1998)) Membranes were resolved by SDS-PAGE on 3–12% linear gradient gels and transferred to nitrocellulose membranes. Immunoblot staining was performed as previously described (Ohlendieck et al., *J. Cell Boil.* 115: 1685–1694 (1991)). Blots were also developed using enhanced chemiluminescence (SuperSignal, Pierce Chemical Co.).

Sucrose Gradient Fractionation of Skeletal Muscle Dystrophin-Glycoprotein Complex.

Skeletal muscle (1.5 g) was dissected from wild-type, Sgca-null and Sgcb-null mice and snap frozen in liquid nitrogen. Frozen tissue was pulverized using a mortar and pestle cooled with liquid nitrogen. The tissues were solubilized by dounce homogenization in 10 ml cold buffer A (50 mM Tris-HCl, pH 7.4, 500 mM NaCl, 1% digitonin) with a cocktail of protease inhibitors (0.6 μg/ml pepstatin A, 0.5 μg/ml aprotinin, 0.5 μg/ml leupetin, 0.1 mM PMSF, 0.75 mM benzamidine, 5 μM calpain inhibitor I, and 5 μM calpeptin). The homogenate was rotated at 4° C. for 1 hr, and subsequently spun at 142,400 g for 37 min at 4° C. The pellets were resolubilized with 5 ml buffer A, rotated at 4° C. for 30 min, and centrifuged as before. The two supernatants were pooled and incubated at 4° C. with WGA-Agarose (Vector Laboratories). The WGA-Agarose was washed extensively in buffer B (50 mM Tris-HCl, pH 7.4, 500 mM NaCl, 0.1% digitonin with the above described cocktail of protease inhibitors) and proteins were eluted with 0.3 M N-acetyl glucosamine (Sigma Chemical Co.) in buffer B. Samples were concentrated to 0.3 ml, diluted 5-fold in buffer B, again concentrated to 0.3 ml using Centricon 30-filters and applied to a 5–30% sucrose gradient at pH 7.4, as described previously (Ervasti et al., *J. Biol. Chem.* 266: 9161–9165 (1991)).

---

What is claimed is:

1. A transgenic knockout mouse whose genome comprises a homozygous disruption in its endogenous β-sarcoglycan gene, wherein said homozygous disruption prevents the expression of a functional β-sarcoglycan protein in cells of the mouse, and wherein said homozygous disruption results in said transgenic knockout mouse exhibiting conditions of: (i) a reduced amount of δ-and ε-sarcoglycan, sarcospan and α-dystroglycan in a smooth muscle, (ii) a disruption of the sarcoglycan-sarcospan complex in a smooth muscle, and (iii) a reduced amount of sarcospan and α-, γ-, -δ, and ε-sarcoglycan in the sarcolemma of a skeletal and a cardiac muscle, compared to the amounts of δ-and ε-sarcoglycan, sarcospan and α-dystroglycan in the smooth muscles, the sarcoglycan-sarcospan complex in the smooth muscles, and sarcospan and α-, γ-, -δ, and ε-sarcoglycan in the sarcolemma of the skeletal and cardiac muscles of a wild type mouse, and wherein said homozygous disruption results in ischemia in said transgenic knockout mouse.

2. The transgenic knockout mouse of claim 1, wherein said homozygous disruption consists of a deletion of a 1606 nucleotides of intron 2 upstream of exon 3, entirety of exons 3–6 and introns 3–5, and 498 nucleotides immediately downstream of exon 6 of the β-sarcoglycan gene, and wherein the deleted portion of the endogenous β-sarcoglycan gene is replaced with a PGK-neomycin resistance cassette.

3. The transgenic knockout mouse of claim 1, wherein the method of making said transgenic knockout mouse comprises:

introducing a DNA construct into a mouse embryonic stem cell, and wherein said DNA construct comprises in order: the first 1800 nucleotides of intron 2 of the β-sarcoglycan gene starting at the 5' end of the intron 2, a DNA sequence encoding a neomycin resistance gene, and 6500 nucleotides starting at 498 nucleotides immediately downstream of exon 6 of the β-sarcoglycan gene, wherein said DNA construct lacks exons 3–6 and introns 3–5 of the β-sarcoglycan gene, wherein the introduction of said DNA construct into said mouse embryonic stem cell results in the disruption of the endogenous β-sarcoglycan gene;

introducing said mouse embryonic stem cell into a mouse blastocyst and transplanting said blastocyst into a pseudopregnant mouse;

allowing said blastocyst to develop into a chimeric mouse whose genome contains the DNA construct;

breeding said chimeric mouse to produce heterozygous offspring;

producing progeny from said heterozygous offspring; and screening said progeny to identify a homozygous transgenic knockout mouse whose genome comprises disruption of the endogenous β-sarcoglycan gene.

4. A smooth muscle, skeletal muscle, or cardiac muscle cell isolated from the transgenic knockout mouse of claim 1, wherein the genome of said smooth muscle, skeletal muscle, or cardiac muscle cell comprises a homozygous disruption in its endogenous β-sarcoglycan gene, wherein said homozygous disruption consists of a deletion of a 1606 nucleotides of intron 2 upstream of exon 3, entirety of exons 3–6 and introns 3–5, and 498 nucleotides immediately downstream of exon 6 of the β-sarcoglycan gene, and wherein the deleted portion of the endogenous β-sarcoglycan gene is replaced with a PGK-neomycin resistance cassette, and wherein said homozygous disruption prevents the expression of a functional β-sarcoglycan protein in said smooth muscle, skeletal muscle, or cardiac muscle cell.

5. A smooth muscle, skeletal muscle, or cardiac muscle cell isolated from the transgenic knockout mouse of claim 2, wherein the genome of said smooth muscle, skeletal muscle, or cardiac muscle cell comprises a homozygous disruption in its endogenous β-sarcoglycan gene, wherein said homozygous disruption consists of a deletion of a 1606 nucleotides of intron 2 upstream of exon 3, entirety of exons 3–6 and introns 3–5, and 498 nucleotides immediately downstream of exon 6 of the β-sarcoglycan gene, and wherein the deleted portion of the endogenous β-sarcoglycan gene is replaced with a PGK-neomycin resistance cassette, and wherein said homozygous disruption prevents the expression of a functional β-sarcoglycan protein in said smooth muscle, skeletal muscle, or cardiac muscle cell.

6. A smooth muscle, skeletal muscle, or cardiac muscle cell isolated from the transgenic knockout mouse of claim 3, wherein the genome of said smooth muscle, skeletal muscle, or cardiac muscle cell comprises a homozygous disruption in its endogenous β-sarcoglycan gene, wherein said homozygous disruption consists of a deletion of a 1606 nucleotides of intron 2 upstream of exon 3, entirety of exons 3–6 and introns 3–5, and 498 nucleotides immediately downstream of exon 6 of the β-sarcoglycan gene, and wherein the deleted portion of the endogenous β-sarcoglycan gene is replaced with a DNA construct wherein said DNA comprises in order: the first 1800 nucleotides of intron 2 of the β-sarcoglycan gene starting at the 5' end of the intron 2, a DNA sequence encoding a neomycin resistance gene, and 6500 nucleotides starting at 498 nucleotides immediately downstream of exon 6 of the β-sarcoglycan gene, wherein said DNA construct lacks exons 3–6 and introns 3–5 of the β-sarcoglycan gene, and wherein said homozygous disruption prevents the expression of a functional β-sarcoglycan protein in said smooth muscle, skeletal muscle, or cardiac muscle cell.

7. A method for identifying a candidate therapeutic compound for the treatment of an individual diagnosed with β-sarcoglycan-deficient limb-girdle muscular dystrophy, comprising:

a) providing a transgenic knockout mouse whose genome comprises a homozygous disruption in its endogenous β-sarcoglycan gene, wherein said homozygous disruption prevents the expression of a functional β-sarcoglycan protein in cells of the transgenic knockout mouse, and wherein said homozygous disruption results in said transgenic knockout mouse exhibiting conditions of: (i) a reduced amount of δ-and ε-sarcoglycan, sarcospan and α-dystroglycan in a smooth muscle, (ii) a disruption of the sarcoglycan-sarcospan complex in a smooth muscle, and (iii) a reduced amount of sarcospan and α-, γ-, δ, and ε-sarcoglycan in the sarcolemma of a skeletal and a cardiac muscle, compared to the amounts of δ-and ε-sarcoglycan, sarcospan and α-dystroglycan in the smooth muscles, the sarcoglycan-sarcospan complex in the smooth muscles, and sarcospan and α-, γ-, δ, and ε-sarcoglycan in the sarcolemma of the skeletal and cardiac muscles of a wild type mouse, and wherein said homozygous disruption results in ischemia in said transgenic knockout mouse;

b) administering the candidate therapeutic compound to the transgenic knockout mouse of step a); and c) assaying the therapeutic effects of the candidate therapeutic compound by comparing the parameters of: (i) a reduced amount of δ-and ε-sarcoglycan, sarcospan and α-dystroglycan in smooth muscles, (ii) a disruption of the sarcoglycan-sarcospan complex in smooth muscles, (iii) a reduced amount of sarcospan and α-, γ-, δ, and ε-sarcoglycan in the sarcolemma of skeletal and cardiac muscles, and (iv) ischemia, in the transgenic knockout mouse which has received the candidate compound as in step b) with the same parameters of a transgenic knockout mouse of step a) which has not received the candidate therapeutic compound, wherein a difference in one or more of the measured parameters of the transgenic knockout mouse of step b) is an indication of a potential therapeutic effect of the candidate therapeutic compound on β-sarcoglycan-deficient limb-girdle muscular dystrophy.

8. The method of claim 7, wherein the administration of said candidate therapeutic compound results in the delivery of the candidate compound to the smooth muscle cells of the transgenic knockout mouse.

9. The method of claim 7, wherein the administration of said candidate therapeutic compound results in the delivery of the candidate compound to the skeletal muscle cells of the transgenic knockout mouse.

10. The method of claim 7, wherein the administration of said candidate therapeutic compound results in the delivery of the candidate compound to the cardiac muscle cells of the transgenic knockout mouse.

11. The method of claim 7, wherein said candidate therapeutic compound is a DNA construct encoding a protein and administration of said DNA construct results in the expression of the protein in the cells of the transgenic knockout mouse.

12. A method of identifying a candidate therapeutic compound for the treatment of ischemic heart disease in an individual caused by a reduced expression of β-sarcoglycan in the vascular smooth muscles of the individual, comprising:

a) providing a transgenic knockout mouse whose genome comprises a homozygous disruption in its endogenous β-sarcoglycan gene, wherein said homozygous disruption prevents the expression of a functional β-sarcoglycan protein in cells of the transgenic knockout mouse, and wherein said homozygous disruption results in said transgenic knockout mouse exhibiting conditions of: (i) a reduced amount of δ-and ε-sarcoglycan, sarcospan and α-dystroglycan in a smooth muscle, (ii) a disruption of the sarcoglycan-sarcospan complex in a smooth muscle, and (iii) a reduced amount of sarcospan and α-, γ-, δ, and ε-sarcoglycan in the sarcolemma of a skeletal and a cardiac muscle, compared to the amounts of δ-and ε-sarcoglycan, sarcospan and α-dystroglycan in the smooth muscles, the sarcoglycan-sarcospan complex in the smooth muscles, and sarcospan and α-, γ-, δ, and ε-sarcoglycan in the sarcolemma of the skeletal and cardiac muscles of a wild type mouse, and wherein said homozygous disruption results in ischemia in said transgenic knockout mouse;

b) administering the candidate therapeutic compound to the transgenic knockout mouse of step a) whereby the candidate compound is delivered to the vascular smooth muscle cells of the mouse; and c) assaying the therapeutic effects of the candidate therapeutic compound by comparing ischemia in the transgenic knockout mouse which has received the candidate compound as in step b) with the ischemia in a transgenic knockout mouse of step a) which has not received the candidate therapeutic compound, and wherein a reduction or a reversal of ischemia in the transgenic knockout mouse of step b) is an indication of a potential therapeutic effect of the candidate therapeutic compound on ischemic heart disease.

13. A method of identifying a candidate therapeutic compound for the prevention of ischemic injury in an individual caused by a reduced expression of β-sarcoglycan in the vascular smooth muscles of the individual, comprising:

a) providing a transgenic knockout mouse whose genome comprises a homozygous disruption in its endogenous β-sarcoglycan gene, wherein said homozygous disruption prevents the expression of a functional β-sarcoglycan protein in cells of the transgenic knockout mouse, and wherein said homozygous disruption results in said transgenic knockout mouse exhibiting conditions of: (i) a reduced amount of δ-and ε-sarcoglycan, sarcospan and α-dystroglycan in a smooth muscle, (ii) a disruption of the sarcoglycan-sarcospan complex in a smooth muscle, and (iii) a reduced amount of sarcospan and α-, γ-, δ, and ε-sarcoglycan in the sarcolemma of skeletal and cardiac muscles, compared to the amounts of δ- and ε-sarcoglycan, sarcospan and α-dystroglycan in the smooth muscles, the sarcoglycan-sarcospan complex in the smooth muscles, and sarcospan and α-, γ-, δ, and ε-sarcoglycan in the sarcolemma of the skeletal and cardiac muscles of a wild type mouse, and wherein said homozygous disruption results in ischemia in said transgenic knockout mouse;

b) administering the candidate therapeutic compound to the transgenic knockout mouse of step a) whereby the candidate compound is delivered to the vascular smooth muscle cells of the mouse; and c) assaying the therapeutic effects of the candidate therapeutic compound by comparing ischemia in the transgenic knockout mouse which has received the candidate compound as in step b) with the ischemia in a transgenic knockout mouse of step a) which has not received the candidate therapeutic compound, and wherein a reduction or a reversal of ischemia in the transgenic knockout mouse of step b) is an indication of a potential preventive effect of the candidate therapeutic compound on ischemic injury.

* * * * *